US005762908A

United States Patent [19]

Schiestl

[11] Patent Number: 5,762,908
[45] Date of Patent: Jun. 9, 1998

[54] PROCESS FOR DETECTING POTENTIAL CARCINOGENS

[75] Inventor: Robert H. Schiestl, Boston, Mass.

[73] Assignee: Harvard College, President and Fellows, Cambridge, Mass.

[21] Appl. No.: 266,014

[22] Filed: Jun. 27, 1994

Related U.S. Application Data

[63] Continuation-in-part of Ser. No. 929,293, Sep. 13, 1992, abandoned, which is a continuation-in-part of Ser. No. 634,008, Dec. 26, 1990, Pat. No. 5,273,880, which is a continuation-in-part of Ser. No. 193,345, May 12, 1988, Pat. No. 4,997,757, which is a continuation-in-part of Ser. No. 137,325, Dec. 23, 1987, abandoned.

[51] Int. Cl.$^6$ .............................. A61K 49/00; C12N 15/06
[52] U.S. Cl. .............................. 424/9.1; 424/9.2; 424/9.8; 435/172.3; 800/2
[58] Field of Search .............................. 800/2; 424/9.1, 424/9.2, 9.8; 435/172.3

[56] References Cited

PUBLICATIONS

Favor et al., 1987, Genetic Research and Recombination 50:219–223.
Brilliant et al., Apr. 1991, Science 252:566–569.
Burkhart et al., Apr. 1991, "Transgenic Mice in Developmental Biology and Toxicology", National Institute of Environmental Health Sciences, Research Triangle Park, North Carolina, Apr. 1–2, p. 21.
Short, "Transgenic Mice in Developmental Biology and Toxicology", National Institute of Environmental Health Science, Research Triangle Park, North Carolina, Apr. 1–2, 1991, p. 22.
Gossen et al., "Transgenic Mice in Developmental Biology and Toxicology", National Institute of Environmental Health Science, Research Triangle Park, North Carolina, Apr. 1–2, 1991, p. 23.
Myhr, "Transgenic Mice in Developmental Biology and Toxicology", National Institute of Environmental Health Science, Research Triangle Park, North Carolina.Apr. 1–2, 1991, p. 24.

*Primary Examiner*—Brian R. Stanton
*Attorney, Agent, or Firm*—Howard J. Greenwald

[57] ABSTRACT

A process is described for the screening of an agent to determine its effect on the frequency of genome rearrangement in mammals. In particular, mice harboring a $p^{un}$ mutation are exposed to an agent of interest and the frequency of genome rearrangement relative to that observed in an unexposed mouse is determined. The relative frequency of rearrangement represents a measure of the effect of the agent on the host animal.

3 Claims, 10 Drawing Sheets

PROCESS FOR DETECTING POTENTIAL CARCINOGENS

CROSS-REFERENCE TO RELATED APPLICATIONS

This is a continuation-in-part application of applicant's patent application Ser. No. 07/929,293, filed on Sep. 13, 1992, now abandoned, which was a continuation-in-part of application Ser. No. 07/1634,008, filed on Dec. 26, 1990, U.S. Pat. No. 5,273,880, which is a continuation-in-part of patent application Ser. No. 07/193,345, filed on May 12, 1988 (now U.S. Pat. No. 4,997,757), which is a continuation-in-part of application 137,325, filed on Dec. 23, 1987, now abandoned.

FIELD OF THE INVENTION

A process for detecting a potential carcinogen in which mice are contacted with a candidate agent and the frequency of genome rearrangement in such mice is then determined.

BACKGROUND OF THE INVENTION

Assays for identifying potential carcinogens are well known to those skilled in the art; see, e.g., U.S. Pat. No. 4,997,757, the entire disclosure of which is hereby incorporated by reference into this specification.

The assay described in U.S. Pat. No. 4,997,757 utilizes a viable strain of the unicellular yeast *Saccharomyces cerevisiae*; and the process of this patent is substantially superior to other potential carcinogen screening assays utilizing yeast or Salmonella.

Cancer is a disease affecting mammals; and an assay utilizing mammals is commonly believed to be superior to assays which utilize non-mammalian beings (such as yeast, or Salmonella). Many in the scientific community place more faith in data generated from mammalian assays than in data generated from non-mammalian assays.

One reason why mammalian assays often are favored is that mammals contain certain enzymes which metabolize xenobiotic agents and sometimes produce carcinogenic metabolites. These enzymes are not present to the same extent and in the same variety in non-mammalian systems; and, thus, to simulate a mammalian system with a non-mammalian assay mammalian liver homogenate must be added during the test. This not only adds a substantial amount of cost and time to the non-mammalian assay, but it is not clear that the mammalian liver homogenate accurately reflects the environment within the body of the mammal.

There are several prior art processes for detecting the presence of carcinogens or potential carcinogens which utilize mammals; these are often referred to as "long term bioassays". In one such process a colony of mice is exposed to an agent and, after a substantial period of time, the occurrence of tumors is noted and evaluated; an example of such a process is disclosed in U.S. Pat. No. 4,736,866 of Leder, the disclosure of which is hereby incorporated into this specification. One of the problems with this type of process is the relatively long period of time which must be allowed for the tumor to develop after the mice have been exposed to the agent; after this period of time, each mouse in the test must be killed and subjected to an autopsy to evaluate the presence of the tumors. Furthermore, in this process, a large number of mice must be used in each test to obtain statistically valid data.

There is another well known assay, the "mouse spot test," which does not require the autopsies of a large number of dead mice. This test is described in a review by J. A. Styles et al. entitled "The mouse spot test, evaluation of its performance in identifying chemical mutagens and carcinogens," Mutation Research 154:183–204 (1985). In this test, a multiplicity of pregnant mice are exposed to the agent to be tested, and the offspring of such mice are then evaluated to determine the presence of spots in their coats; there is some correlation between the presence of such spots and the carcinogenicity of the agent tested. However the correlation is relatively poor.

As is indicated in U.S. Pat. Nos. 4,701,406 and 4,997,757, the well-known Ames assay (which utilizes certain mutant strains of bacteria) has several major disadvantages. In the first place, many classes of carcinogenic compounds consistently show poor responses in the Ames assay; the Ames assay is not very useful for evaluating certain metals, steroid hormones, and chlorinated hydrocarbons which, although they are known to be carcinogens, give very poor responses in such assay. In the second place, the Ames assay is not generally useful for evaluating carcinogenic compounds which are not mutagenic; see, e.g., column 2 of U.S. Pat. No. 4,997,757.

It appears, however, that, notwithstanding the well-known shortcomings of the Ames assay, the mouse spot test is inferior to such assay. Thus, for example, in the aforementioned review of Styles et al., an experiment was described in which 45 known carcinogens and 6 known noncarcinogens were evaluated in both the Ames assay and the mouse spot test. The Ames assay correctly identified 84 percent of these agents; however, the mouse spot test correctly identified only 74 percent of these agents.

As of this time, the most widely used state of the art transgenic mouse assay system is the Stratagene "... Big Blue™ Transgenic Mouse Mutagenesis Assay System," which is marketed by the Strategene Company 11099 North Torrey Pines Road, La Jolla, Calif. According to Stratagene, this system utilizes a transgenic mouse lineage of the inbred strain C57BL/6 such that each cell of every mouse in the line contains multiple copies of a bacteriophage lambda shuttle vector which is approximately 43 kilobases in size. See, e.g., an article by Jon C. Mirsalis et al. entitled "Induction of hepatic mutations in lacI transgenic mice", published in Mutagenesis, volume 8, number 3, pages 265–271 (1993).

The Stratagene system, however, has several distinct shortcomings. In the first place, it does not detect certain powerful carcinogens which are detectable by other assays. Thus, as is indicated in the aforementioned Mirsalis et al. article, transgenic B6C3F1 and C57BL/6 mice containing a lambda shuttle vector that contains a lacI target do not detect the carcinogenic activity of methylmethane sulfonate (a known hepatocarcinogen which does not induce mutations which are detected by the Stratagene assay in the livers of such mice). Thus, another 1993 publication by Mirsalis et al. (J. C. Mirsalis et al., "Effects of nongenotoxic carcinogens on hepatic mutations in lacI transgenic mice," Environmental and Molecular Mutagenesis, volume 21 [Supplement 22]:48) indicates that 5 daily administrations of carbon tetrachloride to such mice produced no increase in hepatic mutant frequency in such mice.

The consensus among those in the molecular toxicology field appears to be that non-genotoxic carcinogens are not detectable by the Stratagene assay system. Thus Daniela Gunz et al. in an article entitled "Can Nongenotoxic Carcinogens Be Detected With the lacI Transgenic Mouse Mutation Assay" disclosed (at page 209) that "The negative results, both for lacI mutations in liver DNA and for the rate of hepatocyte division, show that the non-genotoxic carcinogens investigated do not give rise to a generally increased level of mutations or a sustained general increase in the rate of cell division."

Although it has not yet been reported in the literature, it is known that the Strategene mouse assay system is not very sensitive to ionizing radiation. This is a critical shortcoming, for it is becoming more apparent with each passing day that exposure to ionizing radiation constitutes a major health hazard. Thus, as was stated by J. Thacker (in an article entitled "Radiation induced mutation in mammalian cells at low doses and low dose rates," Advances in Radiation Biology, 16:77–124, 1992), "It is a sobering thought that, more than 60 years after the demonstration by Muller of the mutagenic effect of ionizing radiation, questions concerning the estimation of risk to the human population are still before us. This lack of progress is not through lack of effort but rather through the complexity of the task and the need to develop and refine methods of analysis".

The present annual per person average dose equivalent for the world's population is about 3 mSv (milliSvedberg) with 2.4 mSv coming from natural background and 0.4 to 1 mSv from medical exposure. Furthermore, additional sources of radiation include nuclear power facilities, radiation accidents, and occupational exposure. These additional sources often lead to local radiation doses that can exceed the lethal dose (which causes 50 percent of people to die within 60 days) about 3 Gray (which, for ionizing radiation, is approximately equal to about 3 Svedberg).

Ionizing radiation causes mutations and cancer. The present maximum permissible dose limit for radiation workers is 50 mSv which may ultimately increase the lifetime risk of cancer in these workers by at least about 30%. It should be appreciated, however, that most of the risk estimates for ionizing radiation are calculated by linear extrapolation from high doses from human exposure during nuclear explosions or accidents or from experimental doses for animals to the lower doses to which most of the human population is exposed. The justification for this is taken from the fact that dose-response relationship for radiation induced carcinogenesis seems to be linear without a threshold at least in the range of 0.5–3 Gy (Little 1993, Upton et al. 1992). However, since we are usually exposed to much lower levels of radiation, biomarkers as dosimeters for low level exposure would be extremely useful for risk assessment.

In most cases no increased risk has been detected at exposure levels below 0.1 Gy among A-bomb survivors and individuals exposed to therapeutic irradiation. However, the Oxford childhood survey started in the 1950's has consistently shown about a 2-fold increase in the occurrence of cancer following diagnostic intra-uterine X-ray exposure at doses of approximately 0.02 Gy. This may indicate a higher susceptibility of fetal tissue to radiation. Currently, no genetic endpoint or biomarker in animals or humans is available to detect irradiation doses of or below 20 mGy.

Applicant is aware of only one study which suggests that ionizing radiation doses below 100 mGy may be mutagenic in human lymphoblasts; see, e.g., an article by A. J. Grosovsky et al. entitled "Evidence for linear response for the induction of mutations in human cells by x-ray exposures below 10 rads," Proceedings of the National Academy of Science U.S.A., N82:2092–2095 (1985). However, the results described in this article were obtained by applying 30 daily doses of 10 mGy, and no effect was found with an acute x-ray exposure of 50 mGy.

In applicant's U.S. Pat. No. 4,997,757, an assay system utilizing yeast with certain repeated genetic elements is described. This system is substantially superior to many of the prior art assays, and it has met with substantial commercial success. However, the assay system of this patent is incapable of detecting the toxic effects of ionizing radiation at levels below about 1.0 Gray.

It is an object of this invention to provide a toxicology assay utilizing mice which is capable of detecting the toxic effects of ionizing radiation at does as low as 10 milliGray.

It is another object of this invention to provide a toxicology assay utilizing mice which is capable of detecting the toxic effects mutagenic carcinogens such as, e.g., methyl methane sulfonate, ethyl methane sulfonate, benzo(a)pyrene, ethylnitrosourea, and the like.

It is another object of this invention to provide a toxicology assay utilizing mice which is capable of detecting the toxic effects of nonmutagenic carcinogens such as, e.g., carbon tetrachloride, trichloroethylene, benzene, sodium arsenate, and the like.

It is an object of this invention to provide a mammalian assay for detecting potential carcinogens which utilizes mammals but does not require their autopsy.

It is yet another object of this invention to provide a mammalian assay for detecting potential carcinogens which can be completed in a substantially shorter period of time than that required for long term bioassays.

It yet another object of this invention to provide a mammalian assay for detecting potential carcinogens which, in at least some respects, is more accurate than prior art mammalian assays.

SUMMARY OF THE INVENTION

In accordance with this invention, there is provided a process for detecting a potential carcinogen. In the first step of this process, a mammal which contains a certain repeated genetic element in its haploid genome is provided. This mammal is then exposed to a potential carcinogenic agent. The presence of such repeated genetic element in the animal's haploid genome causes recombination at a rate sufficient to give rise to an identifiable genome rearrangement at a rate of at least about $1 \times 10^{-11}$ occurrences per cell per generation; and, within a relatively short period of time after such exposure, the extent of such genome rearrangement in the mammals is determined.

BRIEF DESCRIPTION OF THE DRAWINGS

The present invention will be more fully understood by reference to the following detailed description thereof, when read in conjunction with the attached drawings, wherein like reference numerals refer to like elements, and wherein.

Figure 8A:
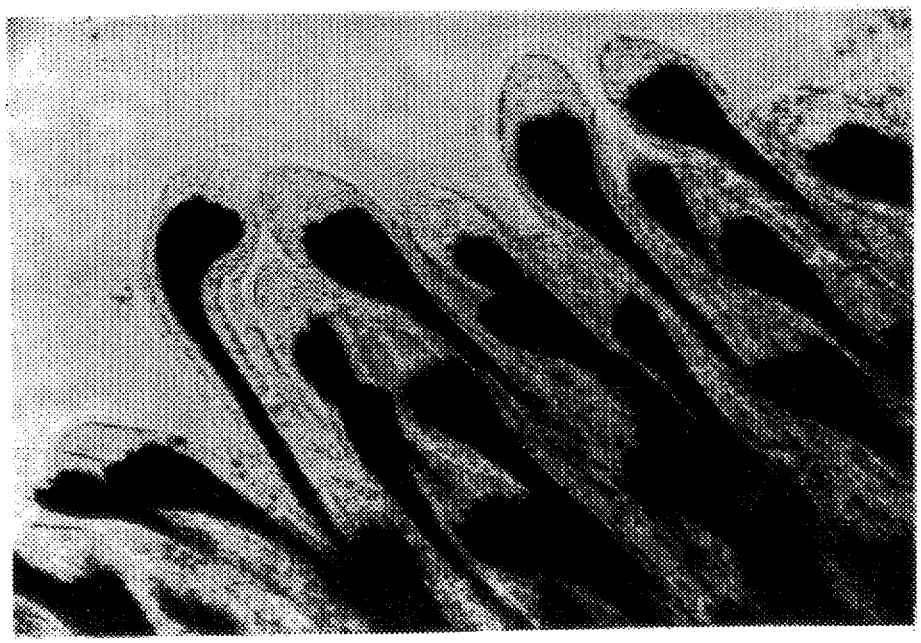
Figure 8B:
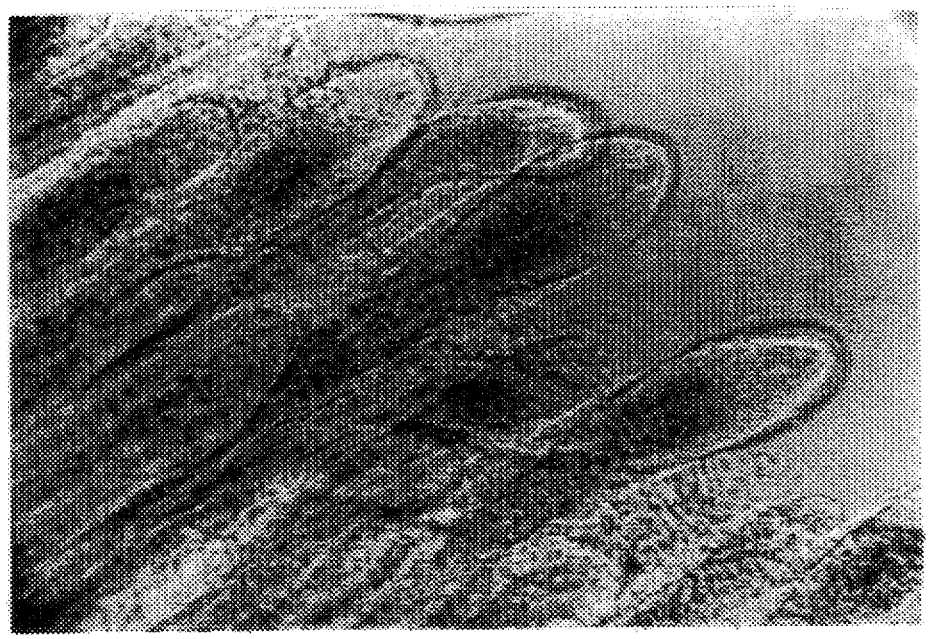
Figure 8C:
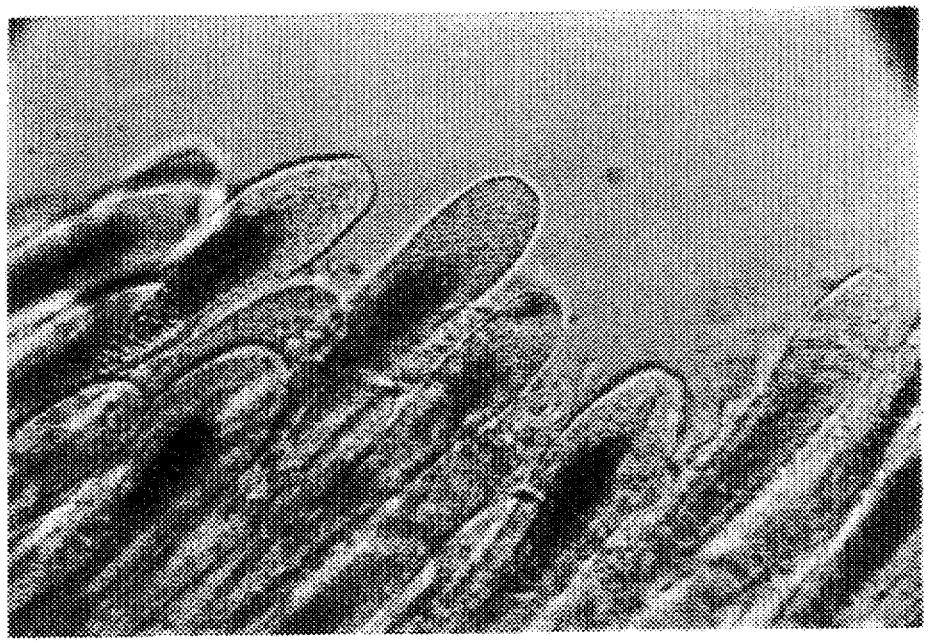
Figure 8D:
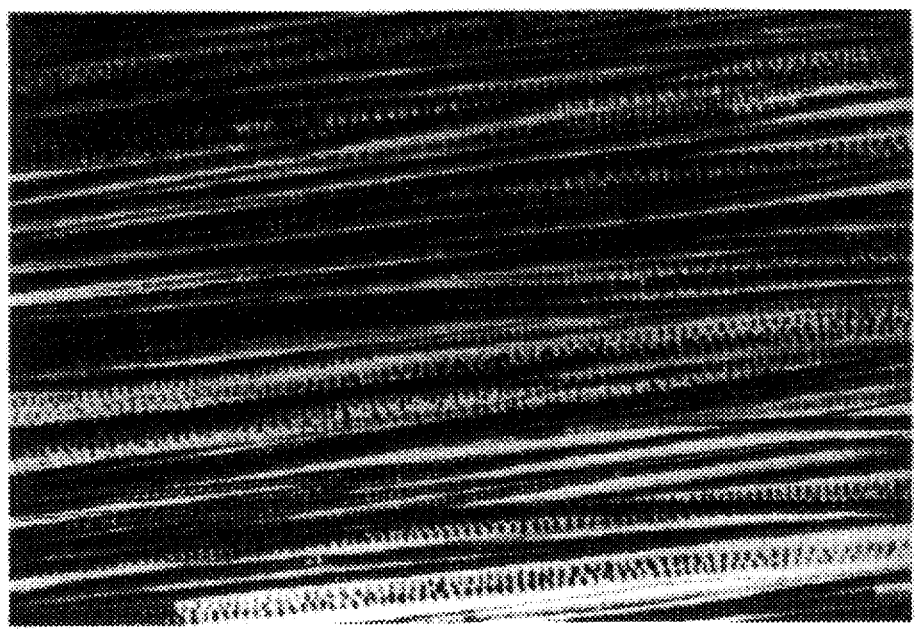
Figure 8E:
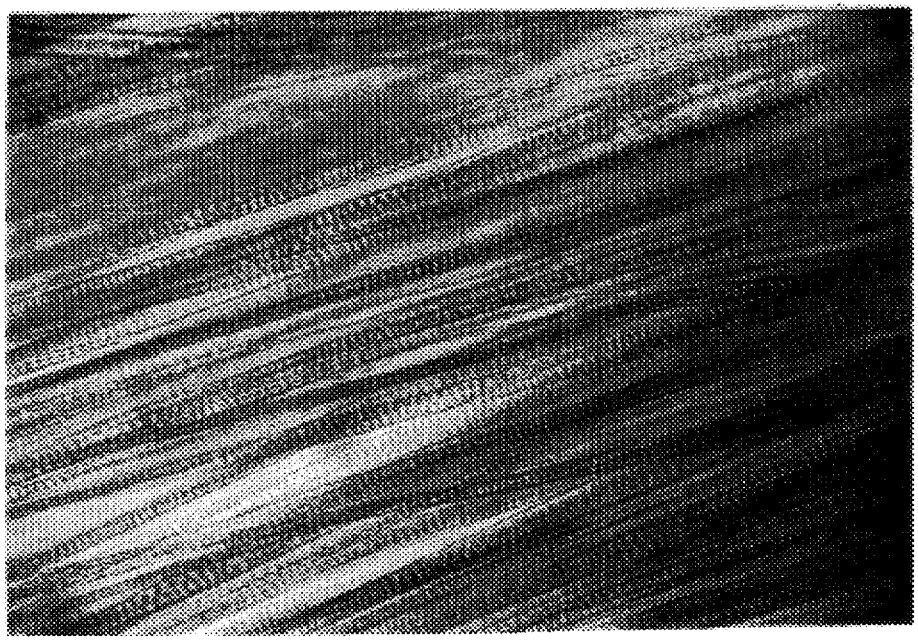
Figure 8F:
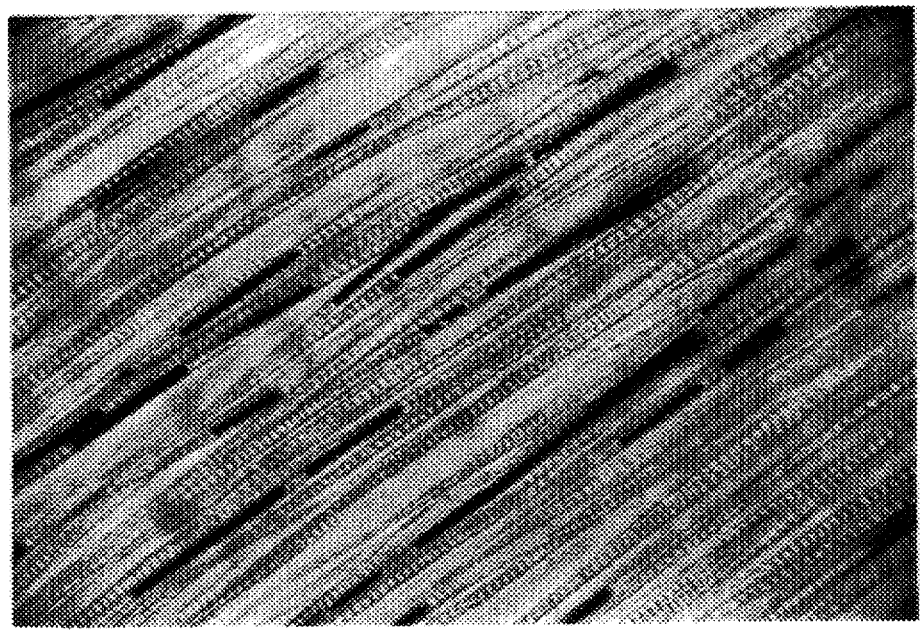
Figure 9:
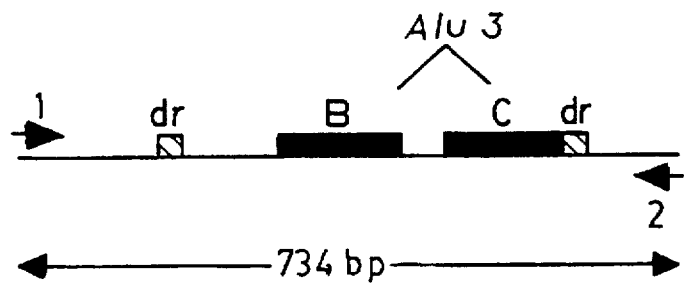
Figure 10:
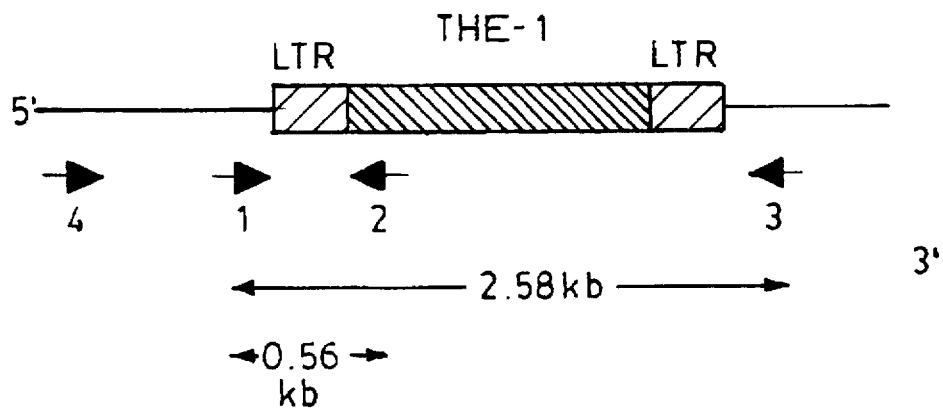
Figure 11:
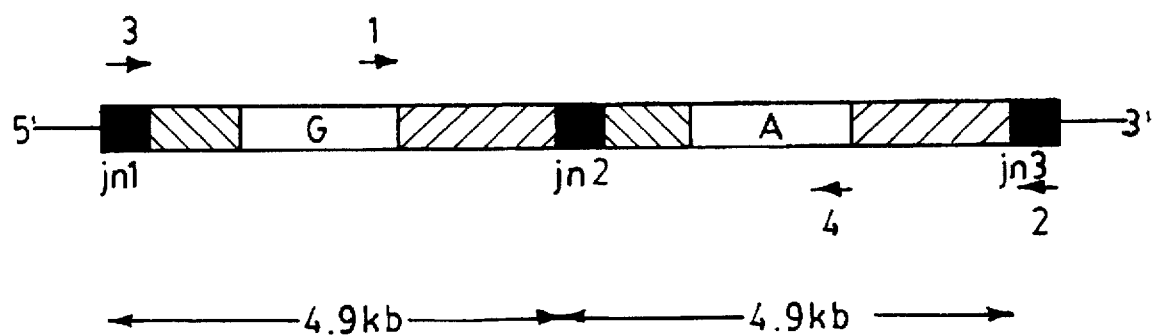

Each of FIGS. 3, 4, 5, 6 and 7 is a schematic illustrating the preparation of a construct which may be used to prepare a mammal for use in applicant's process;

FIGS. 8a, 8b, and 8c are photographs of follicles of the hair of C57BL/6J mice illustrating, respectively, the wild type hair, the p-unstable hair, and the p-unstable hair after irradiation;

FIGS. 8d, 8e, and 8f are photographs of the hair shafts of C57BL/6J mice illustrating, respectively, the wild type hair, the p-unstable hair, and the p-unstable hair after irradiation;

FIG. 9 is a schematic of the upstream region of the human alpha-2 globin gene which carries an Alu repeat sequence;

FIG. 10 is a schematic of the THE-1 sequence;

FIG. 11 is a schematic of the fetal gamma globin gene duplication; and

Figure 12:
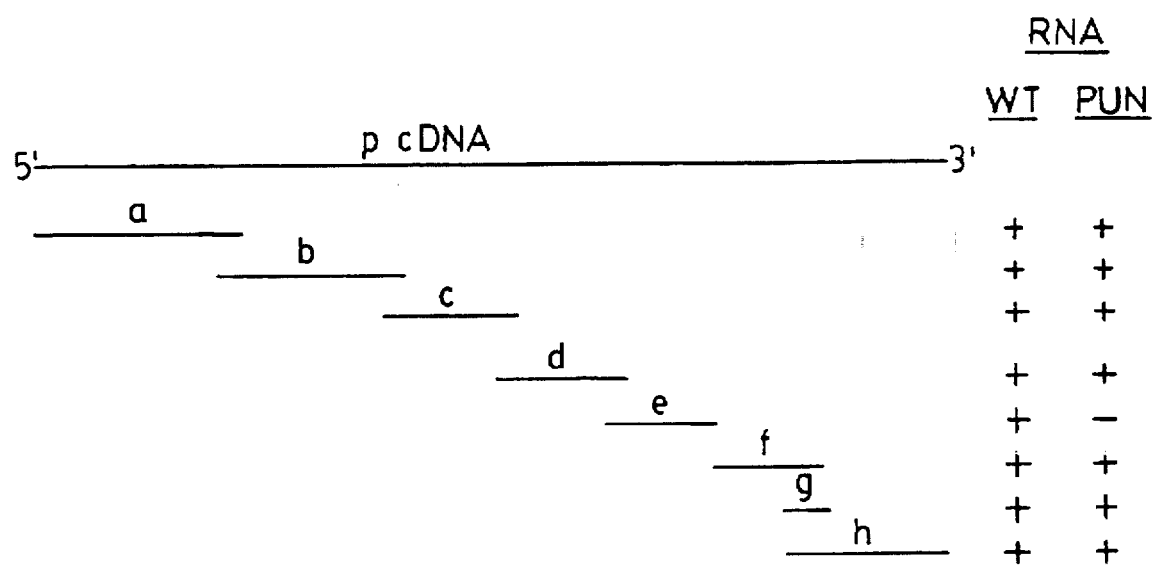

FIG. 12 is a schematic of the cDNA of the pink eyed dilution gene showing different PCR products.

DESCRIPTION OF THE PREFERRED EMBODIMENTS

The present invention provides an assay for identifying potential carcinogens. This assay selects for a genetic endpoint, namely genome rearrangement, which is frequently associated with cancer. The present invention provides a process for screening agents for their activity in increasing the frequency of genome rearrangement in mammals.

The first portion of this part of the specification contains a definition of terms used in describing applicant's process. Many of the terms used in this patent application are well known to those skilled in the art and are used, e.g., in applicant's U.S. Pat. No. 4,997,757, the entire disclosure of which is hereby incorporated by reference into this specification. Thus, by way of illustration and not limitation, the following terms may be used hereinafter:

Allele

Any of one or more alternative forms of a given gene. They occur by mutation, where deletions, substitutions, or insertions have altered the original specific sequence of nucleotides.

DNA repair enzymes

"DNA repair enzymes" recognize the damage caused by genotoxic substances or by other causes (such as spontaneous damage or misreplication) and repair such damage. In the process of repairing the damage, the native DNA sequence of bases is changed. Wherever a change in the DNA sequence has been caused by both the damage and the subsequent repair, a genetic endpoint exists.

Coding region

The "coding region" of a gene is discussed on pages 36 to 46 of the aforementioned book by Watson et al. The coding region of a gene is the DNA sequence which defines the amino acid sequence of the corresponding gene product. A gene product is the protein produced after transcription of a gene and after translation of the transcribed RNA. Transcription is the formation of an RNA copy corresponding to the DNA copy of that gene by RNA polymerase. Translation is the formation of a peptide or protein when the RNA copy is translated into a defined amino acid sequence at the ribosomes. The amino acid sequence is defined by the nucleotide sequence of the DNA.

Crossing over

By way of illustration and not limitation, "crossing over" is a genetic endpoint. Crossing over is reciprocal recombination joining different homologous DNA molecules so that genes combined as A-B and a-b are now arranged A-b and a-B. Crossing over might result from the breaking and reunion between two homologous chromosomes. Homologs are chromosomes that are sufficiently similar to pair during meiosis.

Gene

The unit of hereditary function. It is a DNA (deoxyribonucleic acid) sequence which encodes a functional protein.

Genetic endpoint

As used in this specification, the term "genetic endpoint" refers to the secondary effect of genotoxic substances. Genotoxic substances interact with DNA and thereby change its structure. These substances either can bind to the DNA, can modify one or more bases in the DNA strands, can form adducts with one or more of the bases, can alkylate the DNA, can induce single or double strand breaks, can induce bases adjacent to each other on one DNA strand to pair with each other instead of with the complementary bases on the opposite DNA strand, can intercalate between the stacked bases of the DNA double helix, can cause the DNA strands to bind to each other by other than hydrogen bonds, and the like. These adverse interactions, which are often referred to as lesions, are discussed in U. Goodenough's "Genetics," Third Edition (Saunders College Publishing, New York, 1984.

Genome rearrangement

By way of illustration and not limitation, "genome rearrangement" is another genetic endpoint. A genome is a complete haploid set of chromosomes. A diploid organism has two sets of chromosomes. A genome rearrangement is any genetic event that rearranges the order of genes within a haploid genome or between a haploid genome and other genetic elements, thereby creating a new environment for particular genes either on a different chromosome or on the same chromosome in a different position. Genome rearrangements include, e.g., deletions, translocations, gene amplification, insertions and rearrangements within genes. Deletions identify a loss of any DNA sequence from the genome. A translocation involves the interchange of the position of sequences on nonhomologous chromosomes. Gene amplification is a multiplication of a DNA sequence whereby, e.g., a gene sequence is duplicated, triplicated, etc. Insertions insert DNA sequences of a plasmid virus or DNA fragment into the genome. Intrachromosomal recombination is recombination within one chromosome, either intrachromatid (within one chromatid) or between sister chromatids. Intrachromosomal recombination often causes a genetic endpoint. Interchromosomal recombination is recombination between homologous chromosomes in a diploid cell, and it also often causes a genetic endpoint.

Homology

The degree of identity between the nucleotide sequences of two nucleic acid molecules or the amino acid sequences of two protein molecules. Although sequence determination is the ultimate test of homology, useful estimates can be provided by either DNA-DNA or DNA-RNA hybridization.

Integration

The recombination process which inserts a small DNA molecule into a larger one.

Mutant

A genetic alteration of the wild-type which usually makes the wild-type allele nonfunctional.

Mutation

By way of illustration and not limitation, a "mutation" is a genetic endpoint. As used in this specification, the term mutation refers to a change in a single base pair or in several base pairs. Thus, for example, if one of the bases in a base pair is changed, a lesion occurs, but this is not a mutation within the meaning of this specification; only when both of the complementary base pairs change does a mutation occur. The term mutation, as used in this specification, is equivalent to the term "point mutation" as that term is defined on page 202 of the aforementioned Goodenough book. The base pair may be changed by several mechanisms. One base pair may be changed to another one. Certain chemicals change the chemical identity of one of the bases, the DNA repair or replication enzymes might misread the damaged base, and the enzymes then might modify the heretofore unchanged base.

Plasmid

An extrachromosomal element capable of independent replication.

Recombination

The joining together of two DNA molecules which theretofore had not been joined.

Promoter

A "promoter" is discussed on page 45 of the aforementioned book by Watson et al. The promoter is a DNA sequence in front of the coding region of a gene that RNA polymerase binds to and thus initiates transcription at the startsite. Thus the promoter is required for expression of a functional gene. If the promoter of a gene is lacking, the gene is not expressed and no gene product is made and it falls therefore under the definition of the nonfunctional alleles.

Restriction Enzyme

The term "restriction enzyme," also commonly referred to as "restriction endonuclease," refers to a number of enzymes, derived from a wide range of prokaryotes, that all cleave double-stranded DNA molecules. See, for example, U.S. Pat. Nos. 4,064,011, 4,746,609, 4,808,525, and 4,840,901, the disclosures of each of which is hereby incorporated by reference into this specification. Also see page 207 of John M. Walker et al.'s "The Language of Biotechnology: A Dictionary of Terms" (American Chemical Society, Washington, D.C., 1988).

Sequence homology

"Sequence homology", as defined in this specification means DNA sequence homology and defines regions of DNA sequence which are the same at different locations of the genome, or between different DNA molecules such as between the genome and a plasmid or DNA fragment. As those in the art are aware, the extent of perfect homology is important as definition for homologous sequences. Perfect homology entails the same sequences over some distance in the DNA. As those in the art are aware the length of the distance of perfect homology is important.

Wild-type

The usual or non-mutant form of a gene or organism. This term was originally meant to denote the form in which the organism was found in nature. It has come to have a more specialized meaning, referring to the genetic constitution of an organism at the start of a program of mutagenesis. Chapters 7, 17, and 19 of the aforementioned Goodenough book discuss genetic endpoints. Many of the terms used in this specification are defined in the Goodenough book and also in a text by W. Ralph Singleton entitled "Elementary Genetics", Second Edition (American Book Company, New York, 1962), at pages 537–559. Additionally many of the terms used in this specification are also defined in a book by Benjamin Lewin entitled "Genes IV" published by Oxford University Press, New York, N.Y. Additionally many of the terms used in this specification are also defined in a book by James D. Watson et al. entitled "Recombinant DNA" published by Scientific American Books, New York, N.Y.

DESCRIPTION OF THE PREFERRED EMBODIMENTS

In the process of this invention, a mammal is used which contains a certain repeated genetic element in its haploid genome. The animal's haploid genome causes recombination at a rate sufficient to give rise to an identifiable genome rearrangement at a rate of at least about $1 \times 10^{-11}$ occurrences per cell per generation under ambient conditions.

As is known to those skilled in the art, about 25 percent of the human genome is made up of repetitive DNA sequences which may be either tandem repeats or interspersed repetitive elements and, thus, in the human genome recombination occurs at a rate sufficient to give rise to an identifiable genome rearrangement at a rate of at least about $1 \times 10^{-11}$ occurrences per cell per generation under ambient conditions. See, e.g., an article by Schmid et al. in "Chromosomes: Eukaryotic, Prokaryotic and Viral", Volume 1, CRC Press, Boca Raton, Fla., pp. 3–29 (1989).

Various families and subfamilies of repetitive elements have been identified in the human genome, such as Alu family repeats consisting of short interspersed repeats (W. R. Jelinek et al., "Repetitive sequences in eukaryotic DNA and their expression, Annual Review of Biochemistry, 51:770–771, 1982), the Kpn I family of long interspersed element repeats (M. F. Singer, SINEs and LINES: Highly repeated short and long interspersed sequences in mammalian genomes," Cell 28, 433–434, 1982), transposon-like Human Elements (THE-1 sequences) which belong to the family of retrotransposons (K. E. Paulson et al., "A transposon-like element in human DNA," Nature 335, 400–402, 1985), Long Terminal Repeat (LTR) sequences consisting of short, repetitive elements (Paulson et al., supra, 1985), Long Interspersed Elements (LINE sequences) (Singer, supra, 1982), etc.

Because of the large number of repetitive sequences scattered throughout the human genome, intrachromosomal recombination events between direct repeats may occur widely in the genome (see, e.g. Calabretta et al., "Genome instability in a region of human DNA enriched in Alu repeat sequences," Nature 296:19, 1982) and may lead to various genetic disorders if an essential locus is deleted or disrupted during the process. In fact, various genomic rearrangement events involving deletions have been associated with different abnormalities such as Ataxia Telengiectasia (AT), Prader-Willi Syndrome (PWS), Angelman Syndrome (AS), etc. A considerable portion of the human genome is made up of non-essential DNA sequences or intron regions and deletion events occurring in these regions may go unnoticed in the majority of cases, when not directly linked to a disorder phenotype. However, such loci may serve as useful markers for monitoring deletion recombination events occurring in the genome.

It is well-known that the human genome is similar to all other mammalian genomes inasmuch as all such mammalian genomes are made up of a substantial number of repetitive DNA sequences which may be either tandem repeats or interspersed repetitive elements and, thus, in these mammalian genomes, recombination occurs at a rate sufficient to give rise to an identifiable genome rearrangement at a rate of at least about $1 \times 10^{-11}$ occurrences per cell per generation under ambient conditions. Although the nature of the repetitive DNA sequences may vary from one mammalian genome to another, all of such mammalian genomes contain a sufficient number of families of repetitive DNA sequences which contain members that are sufficiently homologous to recombine with each other at a rate sufficient to give rise to an identifiable genome rearrangement at a rate of at least about $1 \times 10^{-11}$ occurrences per cell per generation under ambient conditions.

Thus, as will be readily apparent to those skilled in the art, in addition to the preferred mouse described in the remainder of this specification, one may use other mice, and/or rats, and/or monkeys, and/or guinea pigs, and/or rabbits, and/or hamsters, and/or human beings, and the like.

In the remainder of this specification, for the sake of simplicity of illustration, reference will be made to the use of a particular species of mouse and of human beings. It should be understood, that other mice and/or other mammals may be used in this process.

Referring again to those mice which preferably are used in the process, several such mice are available. One such mouse is sold by the Jackson Laboratory of 600 Main Street, Bar Harbor, Me. 04609 as product number C57BL/6J-p$^{un}$. This mouse contains a mutation which is known as pink-eyed unstable, and it is listed on page 5.60 in Catalog "Handbook on Genetically Standardized Jax Mice" number S7/82, which was published by Jackson Laboratory in Jul. 1982. This mouse is described in the "Jax Mice" price list published by the Jackson Laboratory on July 1988 as stock No. JR0028. It is also described in the "List of mutations and mutant stocks of the mouse" also published by the Jackson Laboratory in July 1988. A general description of this mutation and other mutations useful in applicants process can be found e.g. in a book by W. K. Silvers entitled "The coat colors of mice" published by Springer Verlag, New York (1979).

The pink-eyed unstable mouse has been described in several literature references. Thus, in an article by M. H. Brilliant et al., "Direct molecular identification of the mouse pink-eyed unstable mutation by genome scanning," Science 252:566–569 (1991) it was disclosed that this mouse showed the highest spontaneous reversion frequency of the pink-eyed unstable mutation ("p$^{un}$") of any mammal. Thus, in an article by R. G. Melvold ("Spontaneous somatic reversion in mice, effects of the parental genotype on the stability at the p-locus," Mutation Research 12:171, 1971), it was disclosed that 3.8 percent of the offspring of these mice had patches of wild-type color in their coat and thus are mosaic revertants. The Melvold article also disclosed that, of these mosaic revertants, about 90 percent have only a very small part (0.01 percent to 2 percent) of their coat affected; 0.4 percent of the offspring had 2 to 30 percent of their coat affected; and 0.26 percent of the offspring had 60 to 100 percent of their coats affected.

The p$^{un}$ mutation which is present in the C57BL/6J-p$^{un}$ mice is a deletion disruption of the pink-eye dilute locus creating a DNA sequence duplication of at least 17.8 kilobases, which is a head to tail duplication; see, e.g., an article by M. H. Brilliant et al., "Direct molecular identification of the mouse pink-eyed unstable mutation by genome scanning," Science 252:566–569 (1991).

Reversion of the p$^{un}$ mutation in the genome of the C57BL/6J-p$^{un}$ mouse is due to a deletion of one copy of the duplicated sequence. The spontaneous frequency of p$^{un}$ reversion is about one in 10,000 cells.

Another such mouse which may be used in the process of this invention is also commercially available from the Jackson Laboratory. This latter mouse is sold by the Jackson Laboratory as Product numbers DBA/1LacJ, DBA/1J, and DBA/2J, each of which contain the mutant allele. It is known as dilute (d$^v$) coat-color mutant DBA mouse and is listed on pages 17 and 18 in Catalog "Handbook on Genetically Standardized Jax Mice" fourth edition, which was published by Jackson Laboratory in Apr. 1991. This mouse is listed in the "Jax Mice" price list on page 7 published by the Jackson Laboratory on Jul. 1988 as strains DBA/1J, DBA/1LacJ and DBA/2J. A general description of this mutation can be found e.g. in the aforementioned book by W. K. Silvers entitled "The coat colors of mice".

This dilute (d$^v$) coat-color mutant DBA mouse has been described by N. G. Copeland et al. ("Excision of the DBA ectopic provirus in dilute coat-color revertants of mice occurs by homologous recombination involving the viral LTRs," Cell 33:379–387, 1983), and P. K. Seperak et al. ("Somatic and germ-line reverse mutation rates of the retrovirus-induced dilute coat-color mutation of DBA mice," Proceedings of the National Academy of Sciences USA 85:189–192, 1988).

In the mammals used in the process of this invention, the genetic elements contained in the haploid genome of the mammal are sufficiently homologous so that, under ambient conditions, and without intentionally exposing the mammal to any suspected carcinogen, the genetic elements recombine with each other at a rate of at least about $1 \times 10^{-9}$ occurrences per cell per generation.

Those skilled in the art are well aware of how to determine whether repeated genetic elements exist in the genome of a mammal which will lead to an identifiable genome rearrangement. First, an indication of the presence of repeated elements in the genome is the fact that they recombine with each other to give rise to genome rearrangements. Genome rearrangements can, for instance, give rise to reversion of a mutation, such as, in the case of the aforementioned C57BL/6J-p$^{un}$ as well as the DBA mice. One characteristic of the reversion events that occur by genome rearrangement may be that they occur at a higher rate than regular reversion events that occur by mutation. Regular germ line mutation events occur about 6.7 times in ten million ($0.67 \times 10^{-6}$) gametes, see e.g. the aforementioned article by Schlager et al. entitled "Spontaneous mutation and mutation rates in the house mouse". The aforementioned p$^{un}$ mutation reverts at a rate of 6.8 times in ($0.68 \times 10^{-3}$) 10,000 gametes, see the aforementioned article by Melvold published in Mutation Research 12:171–174 (1971). Thus, the p$^{un}$ mutation shows a 1000 fold higher germ line reversion rate, by genome rearrangement, compared to other mutation rates. Similarly, the second aforementioned mutation, d$^v$, in DBA mice shows a reversion rate of $3.9 \times 10^{-6}$ events per gamete, again at least a five fold higher rate than other recessive mutation alleles show, see the aforementioned article by Seperack et al. published in Proc. Natl. Acad. Sci. USA 85:189–192. The reversion of the d$^v$ allele is also due to genome rearrangement, see e.g. the aforementioned article by N. G. Copeland et al. published in Cell 33:379–387 (1983). This is also true for somatic reversion rates. Somatic reversions occur in the somatic cells of the animal rather than in the germline. Thus somatic reversion events can be detected in the same animal rather than in its offspring, like for germ line mutations. Spontaneous somatic mutations occur at such a low frequency that they are not amenable to study. However, as disclosed above, the p$^{un}$ allele reverts spontaneously in about 3.8% of the animals and the d$^v$ allele reverts in about one per one million animals, see the aforementioned article by Seperack et al. published in Proc. Natl. Acad. Sci. USA 85:189–192.

As known to those skilled in the art, genome rearrangements and repeated elements can be detected by Southern blotting. As disclosed in the aforementioned article by N. G. Copeland et al. published in Cell 33:379–387 (1983) Southern blotting has been used to determine that the reversion of the d$^v$ mutation occurs by homologous recombination involving the viral LTRs, which results in one form of genome rearrangement. The method of Southern blotting is well known to those skilled in the art and may be found e.g. on pages 127 to 133 in a book by J. D. Watson et al. entitled "Recombinant DNA" published by Scientific American Books/ W. H. Freeman and Company, New York in 1992. Many other recombinant DNA techniques relating to this invention can also be found in the aforementioned book. In principle, the gene that is affected by the mutation and that recombines to give rise to the genome rearrangement is cloned or obtained from the general public domain. DNA is isolated from the mammalian cells before the genome rearrangement happens and after the genome rearrangement happened. This genomic DNA is digested with an appropriate restriction enzyme and the different fragments are separated on an agarose gel. The fragments separated by size are denatured in a buffer and then transferred to a membrane. In the meantime, a fragment of the above gene suspected of being involved in the rearrangement is isolated and radioactively, usually by $^{32}p$ or by $^{35}S$, labeled and subsequently denatured, usually by boiling. The membrane containing the separated denatured DNA fragments is then incubated at about 65° C. with the radioactively labeled probe so that the radioactively labeled single stranded DNA fragments can hybridize with the single stranded fragments on the membrane. This leads to radioactively labeling of the fragments on the membrane that are homologous to the aforementioned radioactively labeled gene suspected of being involved in the genome rearrangement. Thereafter the membrane is subjected to an autoradiography which makes the radioactive fragments visible on X-ray film. If a genome rearrangement occurs the patterns seen for mouse DNA isolated before the rearrangement happened may differ from the DNA isolated after the rearrangement happened. Furthermore, at least with some restriction enzymes and some gene fragments the Southern blot of DNA isolated before the genome rearrangement happened should show two fragments, indicating the repeated genetic elements. In that case, DNA isolated from cells after the genome rearrangement happened digested with the same restriction enzymes and hybridized to the same fragment may show only one fragment. All of these cases should be subject of this invention, if no difference is found, or no repeated elements are found, it is likely that the wrong restriction enzymes or the wrong DNA fragments have been used for this determination.

If the fragment that is repeated to form the repeated elements is not known, as was the case for the $p^{un}$ mutation, genome scanning may be used to find the repeated elements. This method was applied to determine the repeated elements in the $p^{un}$ mutation, see e.g. the aforementioned article by M. H. Brilliant entitled "Direct molecular identification of the mouse pink-eyed unstable mutation by genome scanning. This technique is similar to the DNA fingerprinting technique of Jeffreys et al. (Nature 314:67, 1985) and is based on the aforementioned Southern blotting technique. The difference to the DNA fingerprinting method is that genome scanning uses a repetitive DNA probe of much higher copy number of about 1000 copies per genome, as compared to about 60 per genome for DNA fingerprinting. Therefore, a larger fraction of the genome can be scanned for sequence differences (such as repeated elements). However, without limitation, both techniques may be used to determine the presence of repeated elements.

In the aforementioned article by Brilliant et al., sequence differences between the DNA's from homozygous $p^{un}$ and wildtype mice of the same sex were likely to be related to the $p^{un}$ mutation. This was because the $p^{un}$ mutation arose in, and is maintained on, the same inbred C57BL/6J background. To look for hybridization band differences a hybridization probe was chosen, that was derived from the sequence family encoding the retroviral like intracisternal A particles (IAP's) see e.g. an article by E. L. Kuff et al. published in Adv. in Cancer Research volume 51:183 (1988). Five prominent variant fragments were detected by Southern blot analysis among the DNAs of individual coisogenic mice homozygous for $p^{un}$, wildtype and revertant alleles using an IAP DNA probe. Four of these five variants were correlated with the sex of the mice, but not with a particular p allele. One variant, however, was correlated with the $p^{un}$ allele: a 2.9 kilobasepair long ApaI fragment displayed enhanced hybridization to the IAP probe in DNA from C57BL/6J $p^{un}/p^{un}$ mice relative to DNA's from mice homozygous for the wildtype or revertant alleles. A cloned isolate of the 2.9 kilobasepair long DNA fragment designated p28 was used for subsequent verification of the nature of the repeated elements. To map the p28 sequence a unique sequence fragment of clone p28, designated 28RN, a 390 basepair long DNA fragment of non-IAP sequence, was isolated.

The 28RN probe was able to detect two $p^{un}$ hybridization band variants. The first variant had a hybridization intensity ratio of approximately 2:1, $p^{un}$ DNA:wild-type DNA. The second variant detected by the 28RN probe was an additional SstI fragment in $p^{un}$ DNA that was not found in the wild-type or the revertant DNA. The occurrence of restriction fragments displaying a 2:1, $p^{un}$ DNA:wild-type DNA and the additional SstI fragment in the $p^{un}$ mutant proves that a duplication caused the $p^{un}$ mutation. This confirms the presence of repeated elements. This duplication was further characterized and it was found that at least 17.8 kilobase pairs of DNA have been duplicated. Furthermore this study proves that reversion to the wild-type p allele deletes one copy of the repeated element which represents the genome rearrangement useful in this invention, which can be identified simply by a change in the fur color of the mouse.

The restriction fragment length polymorphism (RFLP) technique, another variation of the Southern blotting technique, can also be used to determine the presence of repeated elements. Those skilled in the art are familiar with the RFLP technique, that is for instance described on pages 525–528 and elsewhere in the aforementioned book by J. D. Watson et al. entitled "Recombinant DNA". With RFLP the DNA of coisogenic mice of wildtype and mutant (presumably containing the repeated elements) are subjected to Southern blots using single copy or multiple copy genetic elements as probes. When a RFLP is detected and its occurrence correlates with the occurrence of the aforementioned mutation then this is an indication for the presence of repeated genetic elements.

By way of illustration, the repeated elements may also be detected using the PCR (polymerase chain reaction) technique which is described, e.g., in U.S. Pat. Nos. 4,683,202, 4,683,195, 4,800,195, and 4,965,188. The disclosure of each of these patents is hereby incorporated into this specification.

As is well known to those skilled in the art, the PCR technique uses oligonucleotides as primers for a heat stable DNA polymerase. These oligonucleotides are designed so that a fragment of DNA can be amplified. Template DNA has to be present so that a fragment can be amplified from that template. The concentration of the template DNA can be very small, it has been shown that even from the DNA of one single cell a fragment can be successfully amplified. In a PCR reaction including nucleotides, template DNA, primers and the heat stable DNA polymerase, for instance Taq polymerase which may be purchased from Perkin Elmer Cetus Corporation of 761 Main Avenue, Norwalk, Conn. 06859. Oligonucleotides can be synthesized with a DNA synthesizer, for instance the Biosearch 8700 synthesizer which can be purchased from New Brunswick Company, Inc. of Edison, N.J. 08818 and operated with chemicals from Milligen/Biosearch, a division of Millipore of 186 Middlesex Turnpike, Burlington, Mass. 01803. All procedures should be followed as described by the aforementioned suppliers. Many uses of the PCR technique can be found, e.g. in the aforementioned book by Watson et al. entitled "Recombinant DNA". The optimization of conditions for PCR can, for instance, be found in a book by Innis, M. A. et al. (1990) entitled "PCR protocols: A guide to methods and applications" published by Academic Press, New York.

By way of illustration, to be useful for determination of the presence of repeated genetic elements the oligonucleotide primers used may be designed so that the amplified fragment includes one junction created by the amplification. Thus, the junction created by the amplification is not present in the DNA from the mammals without the amplification or from those mammalian cells which have undergone genome rearrangement. In this case, the absence of said DNA fragment produced by PCR may indicate a genome rearrangement.

Alternatively, the primers may be designed so that the PCR amplified fragment spans across a novel junction that is created by the genome rearrangement, such that a PCR product is only obtained from cells that underwent said genome rearrangement.

By way of further illustration repeated genetic elements can be detected by DNA sequencing. Those skilled in the art are familiar with the DNA sequencing techniques, that are, e.g., described in the aforementioned book by J. D. Watson et al. entitled "Recombinant DNA". This technique may be especially useful in the future, since automated sequence apparatuses are available. In that way repeated genetic elements are defined by at least two homologous sequences in the haploid genome of a mammal.

Other methods that can identify repeated genetic elements can also be used to determine whether a particular mammal falls within the scope of this invention.

In addition to having a genome with repeated genetic elements which will lead to an identifiable genome rearrangement, the mammal used in the process of this invention also exhibits an extraordinarily high degree of such identifiable genome rearrangement when subjected to a specified carcinogenic agent for a specified period of time. In the test used to evaluate the genome rearrangement, the carcinogenic agent used is gamma radiation. In this test, the mammals to be evaluated are subjected to a dose of 1 Gray ("radiation absorbed doses") per mouse. Thereafter, from about 0 to about 30 days after such irradiation, the mammals are evaluated by conventional means to determine whether an identifiable genome rearrangement has occurred. Those animals which have an identifiable genome rearrangement under the conditions of this test at a rate of at least about 1 in 1,000,000 animals tested and, preferably, at least about 1 in 1,000 animals tested, wherein the frequency of identifiable genome rearrangement caused by the exposure to the radiation is greater than the frequency of spontaneous genome rearrangement, may be used in the process of this invention. It is more preferred that the identifiable genome rearrangement occur in at least once in each 500 animals tested.

In some cases, with radiation sensitive animals, the mammals will die as a result of the radiation prior to the 30 days waiting period. These radiation sensitive mammals are suitable for use in applicant's process.

Those skilled in the art are well aware of how to determine the existence of an identifiable genome rearrangement. Thus, for example, with the pink-eyed unstable mouse, and/or the DBA mouse, one may count the number of mice whose coats contain patches of changed coat color. These mutations show a lighter, more dilute color than the wild-type mice see e.g. the aforementioned papers by Melvold published in Mutation Research 12:171–174 (1971) and by Copeland et al. published in Cell 33:379–387 (1983). Dark patches on the dilute fur will indicate genome rearrangements that occurred at some time during the development of the embryo. The derivative cells from that genome rearrangement divide and give rise to one patch of wild-type color on the fur of the animal. The patches are most easily detected 12 to 14 days after birth because the fur coats of the mice have not yet been fully formed. To record the results pictures of the animals can be taken. Alternatively, the patches can be detected under the microscope. In this way, even single hairs can be evaluated. Similar methodology has been used in the aforementioned "mouse spot test" and has been disclosed, for instance, in an article by Searle et al. entitled "An in vivo method for the detection of somatic mutations at the cellular level in mice" published in Mutation Research 92:205–215 (1982). For this purpose the animal may be sacrificed and its skin removed. Samples of the fur may be prepared to allow examination under the microscope. In this way, many fewer animals have to be examined, since one can count many more (microscopically small) effects of genome rearrangements in one mouse.

By way of illustration, the pink-eyed unstable mutation also affects the retinal pigment epithelium of the mouse, see e.g. an article by M. S. Deol entitled "The effects of the pink-eyed unstable gene on the retinal pigment epithelium of the mouse" published in J. Embryol. exp. Morph. 78:291–298 (1983). Thus, as disclosed in the aforementioned article by M.S. Deol retinal pigmentation can be determined macroscopically by the eye, or microscopically after sacrificing the animals and preparing thin sections of the eyes. Again, with this technique fewer mice may be needed to obtain statistically significant results, since many more patches can be found under the microscope than can be found by normal visual determination.

By way of illustration, one may determine the rate of genome rearrangement by the aforementioned Southern blotting technique. For instance, a fragment of the amplified region may be used as described in the aforementioned article by Brilliant et al. published in Science 252:566–569 (1991). Without limitation, the genome rearrangement may be detectable by a change in the intensity of the hybridizing band in the Southern blot. Furthermore, the genome rearrangement may be detectable by the appearance (or disappearance) of a certain fragment in the Southern blot.

Thus, by way of further illustration, one may determine the rate of genome rearrangement by the aforementioned PCR technique. Without limitation, the primers may be designed so that the PCR amplified fragment spans across a novel junction that is created by the genome rearrangement, so that a PCR product is only obtained from cells that underwent said genome rearrangement. Since PCR is an extremely sensitive method for the detection of certain amplified fragments, this method can, for instance, be used with different tissues of a single mouse. A single mouse or several mice could be sacrificed. The mice could be dissected into different tissues and DNA could be isolated from these tissues. Quantitative PCR could be employed. For this purpose a set of standard primers can be used as controls in multiples of the same reaction. First set of primers should amplify a sequence common in the DNA of a first mouse, that will be tested for the amount of genome rearrangement in its DNA. This control is simply used to verify that PCR works with the isolated DNA and the chosen conditions. A second set of primers only amplifies a sequence from the DNA of a second mouse but not from the DNA of the first mouse. The concentration of DNA from the first mouse at which a fragment that is characteristic for the presence of the genome rearrangement will be recorded. This concentration will be compared to the concentration required to be added of the DNA from the second mouse to obtain an amplified fragment. The amount of rearranged DNA from the first mouse should be roughly equal to the amount of DNA from the second mouse that was necessary to be added. In this way roughly the ratio of rearranged to unrearranged DNA from the first mouse can be determined.

In situ hybridization could also be used to determine the extent of genome rearrangement. For instance, the rearranged gene could be expressed from a strong promoter to be transcribed into a certain species of messenger RNA that is not transcribed in unrearranged cells. Methods for in situ hybridization are well known to those skilled in the art and can be found e.g. on pages 539 to 550 in a book by M. M. Gottesman entitled "Molecular Genetics of mammalian cells" published in Methods in Enzymology volume 151 (1987) by Academic Press, Boston. With in situ hybridization the exact location in different tissues of cells with genome rearrangements could be determined.

Furthermore, one may utilize in situ antibody staining, in which antibodies are caused to interact only with the gene product of those cells which undergo genome rearrangement. This technique is well known to those skilled in the art and is described, e.g., in U.S. Pat. No. 4,968,633, the entire disclosure of which is hereby incorporated by reference into this specification.

By way of further illustration, the chloramphenicol acetyltransferase (CAT) gene could be used to determine the extent of genome rearrangement. As known to those skilled in the art sensitive enzymatic assays for CAT activity exist as described, e.g., on pages 382 to 397 in the aforementioned book by M. M. Gottesman entitled "Molecular genetics of mammalian cells". A transgenic mammal is used for this experiment that contains a construct in which the CAT gene is present in two incomplete parts with overlapping homology or in which the CAT gene is removed from its promoter. In whatever way the construct is designed, the CAT gene should only be expressed after the genome rearrangement occurred. The cells from different tissues of the mammal can be disrupted by sonication of by cycles of freeze-thawing and the cellular debris should be removed by centrifugation. Thereafter CAT activity can be determined from the supernatant. The amount of CAT activity should be proportional to the amount of cells having undergone genome rearrangement.

The lacZ gene of Escherichia coli encodes beta-galactosidase. As known to those skilled in the art the lacZ gene is used for many purposes in molecular biology to study gene expression. The expression of the lacZ gene can be determined, for instance, by the white to blue color method. This method relies on the fact that 5-Bromo-4-chloro-3-indolyl-beta-D-galactopyranoside (known as X-GAL) changes in color from colorless to dark blue when incubated with beta-galactosidase, the product of the lacZ gene. Use of the lacZ gene in molecular biology can, for instance, be found in the aforementioned book by J. D. Watson. X-GAL is commercially available from many sources, for instance, from Sigma Chemical Company of St. Louis, Mo. Since X-GAL readily diffuses through membranes and is not toxic, it can be used to detect those cells that express the lacZ gene, they turn blue. It has also been shown that it can be used in mammalian cells to identify those cells that express the lacZ gene. This has, for instance been shown by D. G. Brenner et al. in an article entitled "Analysis of mammalian cell genetic regulation in situ by using retrovirus-derived "portable exons" carrying the Escherichia coli lacZ gene" published in Proc. Natl. Acad. Sci. USA 86:5517 to 5521 (1989). Thus, the lacZ gene could be used in applicants process. A transgenic mammal is used for this experiment that contains a construct in which the lacZ gene is present in two incomplete parts with overlapping homology or in which the lacZ gene is removed from its promoter. In whatever way the construct is designed, the lacZ gene should only be expressed after the genome rearrangement occurred. After the mice are sacrificed they can either be dissected or they can be mounted and thin sections can be sliced with the proper techniques and equipment. Thus the expression of the lacZ gene can be detected in the cells that underwent rearrangement by a change of the color to blue. Some of the techniques useful for this application may be found, e.g. in an article by J. Zakany et al. entitled "The use of lacZ gene fusions in the studies of mammalian development: developmental regulation of mammalian homeobox genes in the CNS" published in the Journal de Physiologie 84:21–26 (1990). As will be apparent to those skilled in the art, the use of such lacZ gene fusions, and similar systems, allows one to readily detect genome rearrangements in virtually any animal tissue.

By way of further illustration, another way to detect the occurrence of genome rearrangements is by fluorescence-activated cell sorting (FACS). This technique is well known to those skilled in the art and is disclosed, e.g., in the aforementioned book by M. M. Gottesman entitled "Molecular Genetics of mammalian cells". The method utilizes the fact that cells that emit fluorescent light can be counted in a FACS machine. Antibodies can be isolated against a product which is expressed only in those cells that underwent genome rearrangement. For instance, antibodies can be made against the beta-galactosidase; the product of the aforementioned lacZ gene and the aforementioned animal with a lacZ construct may be useful for this purpose. The use of the lacZ gene in this context is, for instance, disclosed in an article by G. P. Nolan et al. entitled "Fluorescence-activated cell analysis and sorting of viable mammalian cells based on beta-D-galactosidase activity after transduction of Escherichia coli lacZ" published in Proc. Natl. Acad. Sci. USA 85:2603–2607 (1988). The antibody is conjugated to a fluorescence emitting dye, so that, when the antibody binds to the cells that underwent genome rearrangement those cells start to emit fluorescence. The animal containing said lacZ construct can be sacrificed, different tissues can be isolated and the cells obtained. These cells can be incubated with the anti-body that only labels those cells that underwent genome rearrangement. Thereafter, the cells that underwent genome rearrangement can be counted in a FACS.

By way of further illustration, one may use in situ PCR (polymerase chain reaction) to quantify the frequency of genome rearrangement within the genome of a mammal. As is known to those skilled in the art, in situ PCR is used to amplify nucleic acids that hybridize to the primers used in the reaction so that amplification will only occur within those cells in which genome rearrangement occurred. See, e.g., U.S. Pat. Nos. 5,021,335 and 5,028,525, the disclosures of which are hereby incorporated by reference into this specification.

Figure 1:
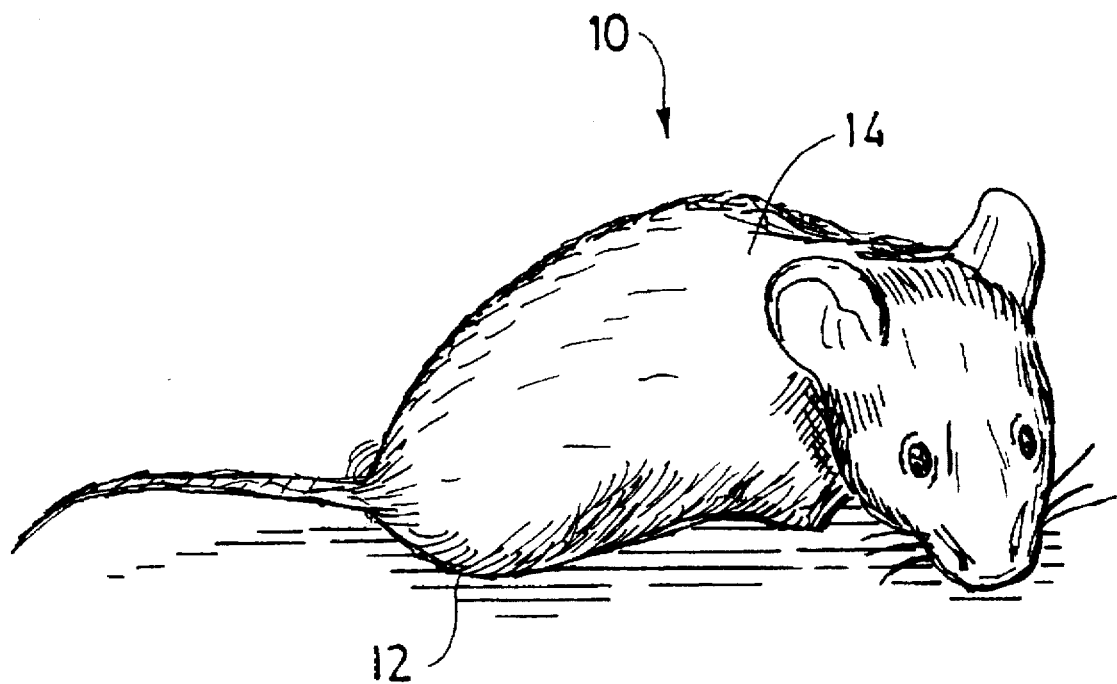
FIG. 1 is a perspective view of one preferred mammal which may be used in the process of this invention.

FIG. 1 illustrates one preferred mouse 10, the aforementioned pink-eyed unstable mouse, which can be used in applicant's process. The mouse 10 illustrated in FIG. 1 has undergone genome rearrangement which caused a change in its coat; note the presence of patches 12 on coat 14.

Figure 2:
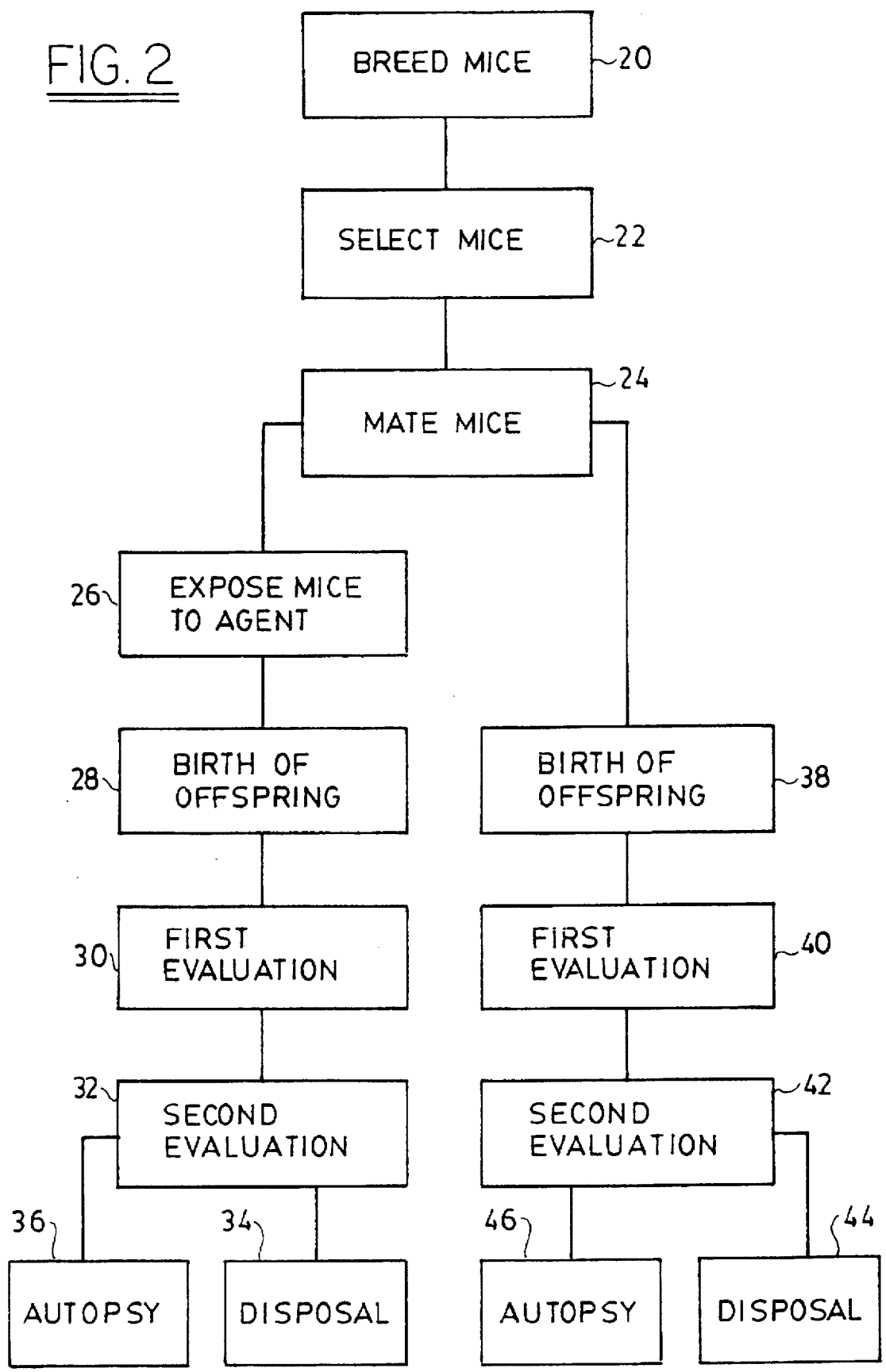
FIG. 2 is a flow diagram illustrating a preferred process of this invention.

FIG. 2 is a flow diagram illustrating one preferred process of applicant's invention. This diagram illustrates a preferred process with the pink-eyed unstable mouse; it will be apparent to those skilled in the art that similar processes can be used with other mammals. Many of the procedures for breeding and experimentation with mice can, for instance, be found in the book by "The Staff of the Jackson Laboratory" entitled "Biology of the Laboratory Mouse" published by Dover Publications, Inc., New York.

Referring to FIG. 2, to in the first step 20 the mice used in the preferred process of the invention are bred. Typically, female and male mice obtained as catalog number C57BL/6J-p$^{un}$ from the Jackson Laboratory are placed in a breeding cage. Generally, one male and from one to three females will be placed in each cage. In one embodiment, one male and one female are placed in each cage.

The offspring produced in the breeding operation are allowed to stay with their parents for three weeks. Thereafter, they are removed from the cage and either used for further breeding (where additional mice are needed for the experiment) or selected in step 22. In general, it is preferred to use about 100 mice for the experiment.

The mice bred in step 20 are selected in step 22 and mated in step 24. It is important, for each mouse couple, to determine the time of mating. This can be done by visually examining the vaginas of the female mice and identifying the presence of a vaginal plug. When the presence of such a vaginal plug is noted, it is to be assumed that mating occurred in the morning hours of the day on which the plug is found.

It is preferred that, from about 8 to about 12 days after the mating occurs for each couple, the female mouse is then exposed to the agent to be tested in step 26. The number of precursor cells is relatively small at the 8th day and becomes much larger at the 12th day; at day 10.25, about 150 to 200 melanocyte precursors are present. It is thus preferred to expose the pregnant mouse to the agent to be tested between the 10th and the 12th days and, more prefer ably, on the 11th day. It will be apparent to those skilled in the art that the precise time of exposure for the pregnant mice is, to some extent, a matter of choice and that other periods for the exposure may also be used. If the mouse is treated on the 8th day, the offspring tend to have fewer but larger patches. On the other hand, the offspring of the mice treated on the 12th day have smaller patches.

The exposed female mice are then placed in a cage and allowed to have their offspring. In step 28, the date of birth of each offspring is noted; it usually is about 30 days after conception.

The offspring from step 28 are visually inspected in step 30 from about 12 to 14 days after birth for the occurrence of patches in their coats; at this time, the presence of spots are most easily discernible, for the fur coats of the mice have not yet been fully formed.

The offspring from step 28 are then subjected to a second visual inspection in step 32 from about 4 to about 5 weeks after their birth; and the presence of patches in their coats is again determined. Thereafter, the majority of the mice from step 32 may be disposed of in step 34. A small percentage of such mice may be subjected to an autopsy in step 36 to determine whether there are any tumors in the mice.

The number of mice showing patches on their fur, the number of patches per mouse, and the size of the patches, are determined at the first evaluation and the second evaluation. A similar control experiment may be performed with mice from step 24 which omits the exposure step 26; in this control experiment, offspring are born in step 38, a first evaluation is conducted in step 40, a second evaluation in conducted in step 42, some of the mice from step 42 may be disposed of in step 44, and some of such mice may be subjected to an autopsy in step 46.

Once the experiments have been conducted, one may determine to what extent, if any, the number of patches in the mice was increased due to the exposure step 26.

It will be apparent to those skilled in the art that many other similar experimental designs may be used to evaluate the agent to be screened.

Thus, e.g., in another experimental design, the effect of the agent is determined by the aforementioned PCR technique. Referring to FIG. 2, the mice exposed in step 26 are sacrificed after such exposure and thereafter they are dissected into different tissues and DNA is isolated from these tissues. As described above a specific PCR product is to be expected after genome rearrangement has occurred. The ratio of unrearranged to rearranged PCR product can be determined for mice exposed to the agent to be tested compared with control mice that were not exposed.

Using PCR, and/or the aforementioned in situ PCR technique, one could, for instance, use mice at all different developmental stages and in different tissues. Therefore, the detection is not limited to the increase of the frequency of genome rearrangement in the embryo and/or in the fur tissue as described above for the macroscopic evaluation of patches in the fur. Therefore, with the PCR technique tissue specific effects of different chemicals can be determined. For instance many tissue specific, especially liver specific carcinogens are known, see e.g. a book by H. A. Milman et al. entitled "Handbook of carcinogen testing" published in 1985 by Noyes Publications, New Jersey. These carcinogens do not seem to show much, if any, effect on other tissues and may be missed with the aforementioned assay detecting patches in the fur.

By way of further illustration, any of the other aforementioned methods for detecting genome rearrangements may be used to quantify the frequency of genome rearrangements in animals exposed to the agents to be tested compared with the frequency of genome rearrangement in control animals without exposure. Without limitation, for these experiments the process of FIG. 2 may be used together with the specific aforementioned techniques to detect genome rearrangements.

Genome rearrangements may also be useful as cell lineage markers. In the development of a multicellular organism different cells develop into different tissues or parts of tissues after proliferation. It is important to know which cells developed into which tissue. Some of the technology used for this application can be found, for instance in the aforementioned article by J. Zakany et al. published in Journal de Physiologie 84:21–26. Genome rearrangement occurs at a certain frequency and all derivative cells contain a genome rearrangement that are descendants of one early cell that has undergone genome rearrangement. Thus these cells descending from one single cell can be distinguished from the other surrounding cells. Hence, applicant's process may be used to provide a cell lineage marker. All of the aforementioned methods for the detection of genome rearrangement (but particularly the aforementioned in situ hybridization technique and the technique using the LacZ gene) are more useful for this purpose.

Preparation of other mammals which may be used in the process

It will be apparent to those skilled in the art that other mammals may be used in applicant's process. Thus, by way of illustration and not limitation, a mouse which contains certain repeated genetic elements may be used in the process.

FIGS. 3 to 7 illustrate, by way of illustration and not limitation, certain repeated genetic elements which may be used in the mammals. Mammalian cells can be constructed with the techniques discussed hereinafter and/or with conventional techniques. If these mammalian cells are embryonic stem cells, then, as disclosed hereafter, an entire transgenic animal can be bred from said cells. This transgenic animal is useful in applicant's process.

It is feasible to culture mammalian cells outside the mammalian body, and this technique is now being used in many laboratories. See, e.g., the books entitled "Animal cell culture: A practical approach" by R. I. Frishney, IRL Press, Washington, D.C. and "Molecular genetics of mammalian cells" in Methods in Enzymology, Vol. 151 by M. M. Gottesman, Academic Press, New York.

Several different sources of mammalian cells can be used in this process such as, e.g., human, monkey, mouse, rat or hamster cells. For a characterization of useful cell lines, see pages 3 to 84 of the aforementioned book "Molecular genetics of mammalian cells" by Gottesman. At the present time, mouse embryonic stem cells are most preferred for use in applicant's process. As known to those skilled in the art, mouse embryonic stem cells can be used to derive an entire animal from a single cell; see, e.g., a book entitled "Transgenic animals" by F. Grosfeld et al. published by Academic Press, San Diego (1992).

As used throughout this specification, the term "repeated genetic elements", as used in connection with alleles, refers to the presence of at least two homologous elements in the haploid genome. Thus, by way of illustration, mammalian chromosomes normally only contain one Hprt gene coding for the hypoxanthine-guanine phosphoribosyltransferase. In order to be used in the process of this invention, the mammalian chromosomes should contain at least one part of the HPRT (or other) genes duplicated in the haploid genome.

By way of further illustration, one of the classes of homologous elements which can be used is the two alleles of one gene. The alleles may be either functional or nonfunctional. When nonfunctional alleles are used, they may interact by recombination with each other, thereby giving rise to at least one functional allele which can be selected for. When two functional or nonfunctional alleles are used, they may also interact by recombination with each other; by way of illustration, two functional or nonfunctional alleles may recombine with each other to delete the region between the two alleles which can be selected against. In either case, the homologous alleles recombine to create a genome rearrangement. It should also be noted that, regardless of which homologous elements are used, they must recombine to give rise to a genome rearrangement.

One class of homologous elements which can be used includes at least two alleles, at least one of which is nonfunctional, and/or at least one of which is functional.

Figure 3:
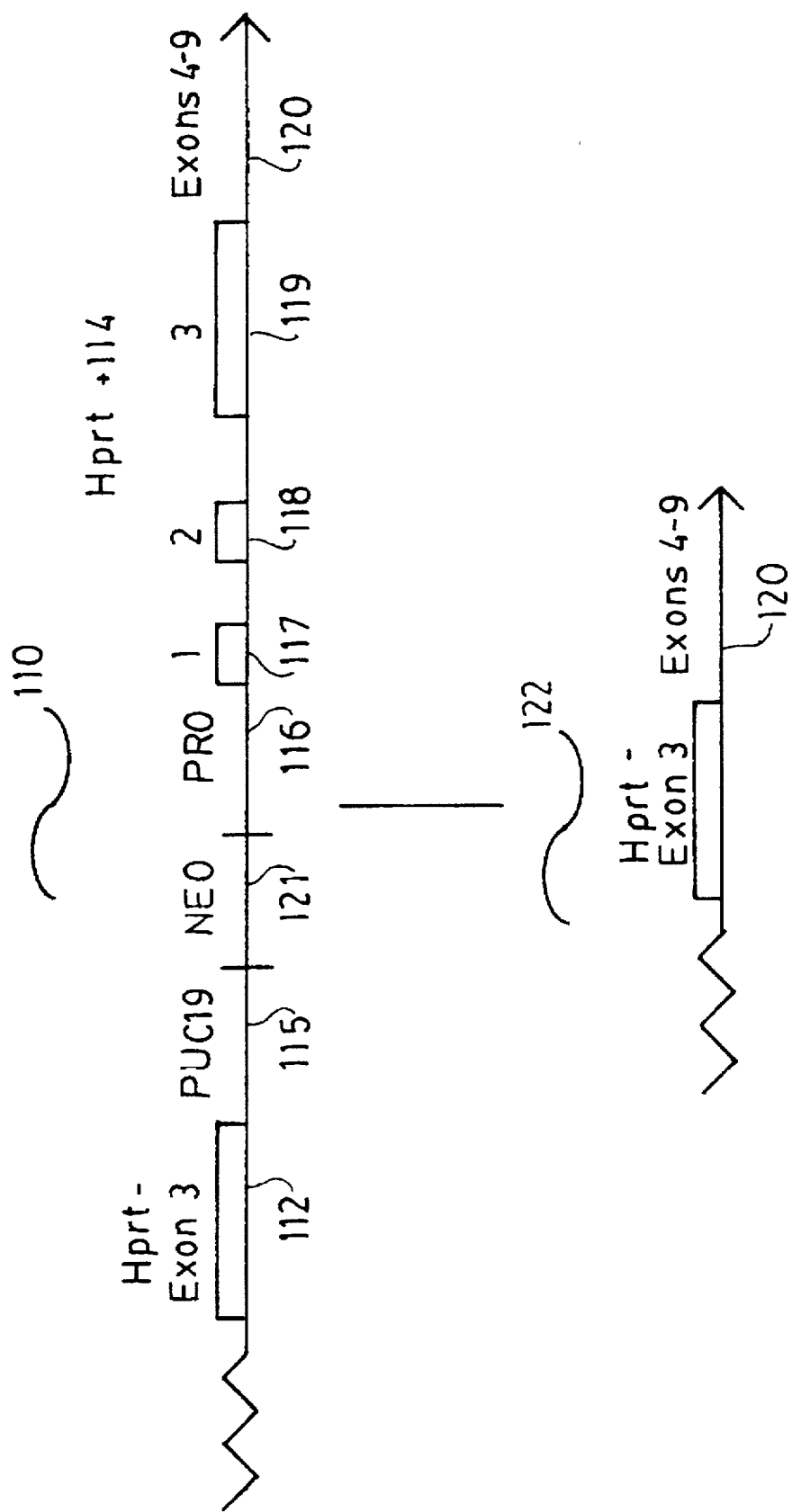

FIG. 3 illustrates one class of homologous elements which can be present in the mammalian cells used in applicant's process. Referring to FIG. 3, construct 110 is comprised of Hprt– allele 112, the homologous Hprt– allele 114. A normal HPRT gene consists of a promoter and exons 1 to 9. The Hprt allele 112 is nonfunctional (Hprt–) and consists only of exon 3 of the Hprt gene. The HPRT allele 114 is functional (HPRT+) and consists of a promoter (116) and exons 1 (117), exon 2 (118) exon 3 (119) and exons 4 to 9 (120). Between Hprt alleles 112 and 114 sequences of the vector PUC19 (115) and the NEO gene (121) are present. Both the PUC19 vector and the NEO gene may not be essential for this process and may be omitted or replaced without any adverse effect.

The construct of FIG. 3 is only one of many within the scope of this invention which can utilize at least two alleles. Thus, by way of illustration and not limitation, alleles 112 and 114 may be the thymidinekinase gene Tk the lacZ gene and the like.

In the construct of FIG. 3, a mutation may be present. The mutation causes the cell line to gain sensitivities or resistance to the selection medium which changes the resistance of the wild type. Thus, referring to FIG. 3, construct 110 contains a functional and a nonfunctional Hprt gene so that the cell line grows in the presence of hypoxanthine, aminopterine and thymidine. When the system used in applicant's invention is constructed, gene 114 is selected for to give rise to construct 110. In this process, a spontaneous deletion is corrected. By way of illustration, as shown in FIG. 3, the Hprt gene is corrected. This selection process will be illustrated later in this specification and can be carried out with any other gene which can be selected against such as Tk or the like.

Construct 110 spontaneously reverts to its mutant form 122 under ambient conditions. Thus, for example, a construct which is identical to construct 110, reverts to the Hprt– gene 122 at a frequency of about $8 \times 10^{-7}$ occurrences per cell. The only difference to construct 110 is that the published construct lacks the NEO gene 121. This cell line, lacking the NEO gene 121, has been designated "E14TG2a with pNMR133" and has been constructed by Doetschman et al. and published in Nature (1987) volume 320 pages 576 to 578. Another cell line also lacking the NEO gene and being similar to pNMR133 has been published in an article by Thompson et al. 1989 in Cell, vol. 56 on pages 313–321. Both of those constructs are readily available to those skilled in the art.

One can measure the rate of reversion of HPRT+ to Hprt– by means well known to those skilled in the art. Thus, for example, one can plate certain numbers of cells on a medium containing 6-thioguanine (6-TG). This and other mammalian genetics methods are described in detail in the aforementioned publication by M. M. Gottesman and the one by R. I. Frishney.

In one of the preferred embodiments of this invention, illustrated in FIG. 3, the viable mammalian cells contain repeated genetic elements which recombine to give rise to an identifiable deletion at a rate of at least about $1 \times 10^{-11}$ occurrences per cell per generation, as measured in accordance with the procedure described in the above references.

The term "identifiable" refers to a rearrangement which, when the cells in which it is present are growing in a suitable selection medium, cause the cells to exhibit some phenotype which is different from that of cells which have not undergone rearrangement. Thus, by way of illustration, if the genome rearrangement causes the cells to form countable and/or visible colonies, the rearrangement is identifiable if cells which have not undergone the rearrangement do not form countable and/or visible colonies in the selection medium, or if the cells which have not undergone said rearrangement form colonies which are distinguishable in any means from the colonies formed by the cells which have undergone said rearrangement. Thus, by way of illustration, if the genome rearrangement causes the cells to form colonies identifiable by different color from the colonies which have not undergone the rearrangement, the rearrangement is identifiable, like in the case of the above mentioned lacZ gene. Thus, by way of illustration and not limitation, if the genome rearrangement causes the cells to grow, the growth of these cells in selection medium may be measured (if adapted to mammalian cells) by techniques similar to the ones described in U.S. Pat. No. 4,256,832 of Findl et al. (which technique detects oxygen consumption of growing cultures), and this growth is thus identifiable. Thus, by way of illustration and not limitation, one adaptation to mammalian cells may be measuring the acidification of the medium by color change or other changes instead of measuring the oxygen consumption.

Referring again to FIG. 3, if construct 110, in the presence of the medium to be discussed later on, reverts to gene 122 in the presence of a toxic agent at a rate substantially higher than $5 \times 10^{-7}$ occurrences per cell per generation, then the chemical induces the recombination mechanism tested for.

Figure 4:
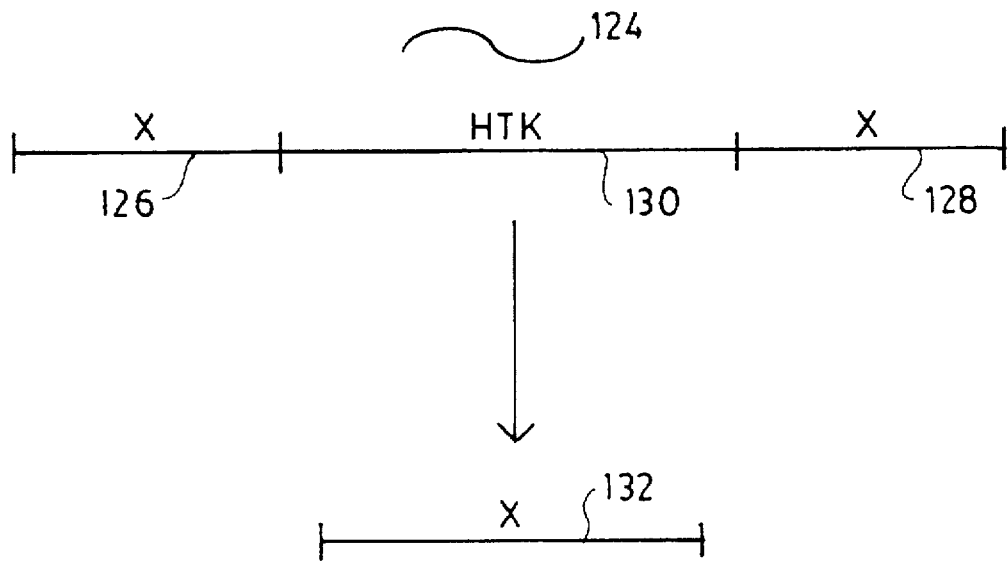

In the embodiment illustrated in FIG. 4, a construct 124 which contains two homologous genetic elements 126 and 128 is shown. Genetic elements 126 and 128 can be—but need not be—alleles or genes; any genetic elements which have sufficient homology with each other to recombine can be used as elements 126 and 128. Thus, by way of illustration and not limitation, one can use any of the aforementioned genes, any DNA sequence which has enough homology to recombine, any cloned gene and the like.

Referring again to FIG. 4, the recombination occurs and deletes the allele 130. Allele 130 must be capable of being selected against so that elements 126 and 128 can recombine to form structure 132 which contains only one copy of the recombination of elements 126 and 128 which contains all or part of the genetic information of element 126 and/or all or part of the genetic information of element 128.

By way of illustration, allele 130 can be the HTK gene. When this HTK gene is present in construct 124, the cell line containing this construct is unable to grow in a medium containing hypoxanthine and bromodeoxyuridine (HBu medium). Under ambient conditions, alleles 126 and 128 recombine with each other to form a deletion of the HTK+ gene, thereby producing allele 132. After recombination, however, the strain containing allele 132 is able to grow in or on Hbu medium. In the embodiment of this Figure, the deletion of one sequence is selected for. The recombination occurs at a specified rate, which can be determined by methods to be discussed later on in this specification.

Other wild type allele 130's can also be used. Thus, for example, instead of the HTK gene, one can also use HPRT and the like. When, for example, a cell line containing the HPRT allele as allele 130 in construct 124, then the strain is unable to grow in a medium containing 6-thioguanine. As before, the alleles 126 and 128 recombine with each other to produce allele 132, and the cell line containing allele 132 is able to grow in the presence of 6-thioguanine.

With regard to the embodiment illustrated in FIG. 4, applicant has discussed the TK, and HPRT alleles 130. However, as those skilled in the art are aware, other genes can be used as long as they can be selected against with the use of a specified medium. These other genes and media are within the scope of this invention.

Figure 5:
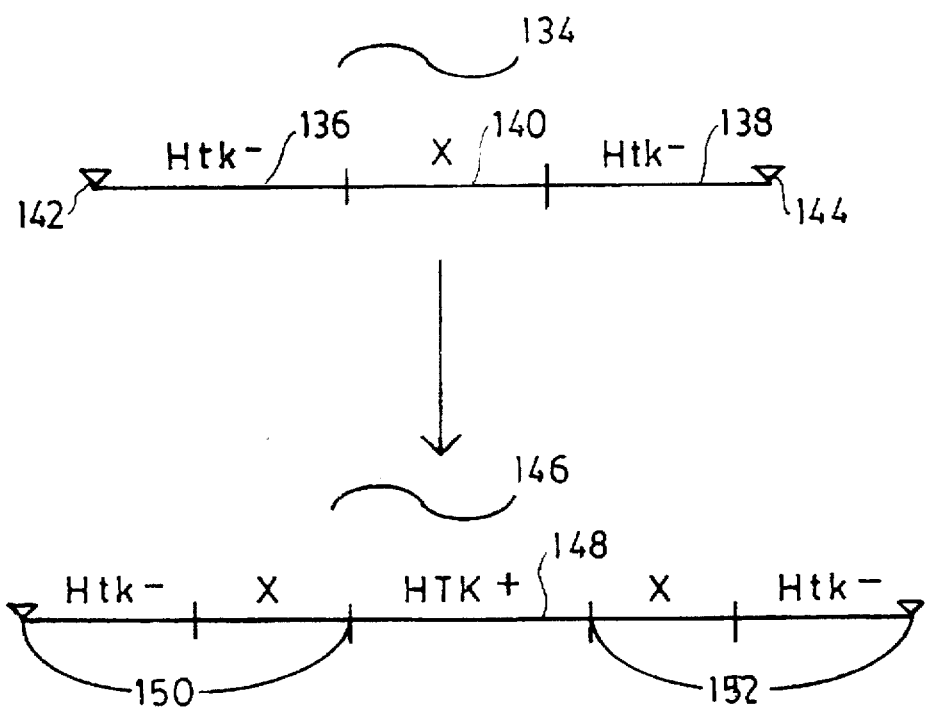

In the embodiment illustrated in FIG. 5, a construct 134 is illustrated which is comprised of two nonfunctional alleles, 136 and 138 and spacer DNA 140. As used in this specification, the term spacer DNA refers to any sequence of DNA which serves as a spacer between two repeated homologous elements. Points 142 and 144 indicate where deletions are present in the nonfunctional alleles. Thus, referring to the particular embodiment illustrated in FIG. 5, construct 134 is comprised of Htk–136, the homologous Htk–138, and the spacer DNA 140; points 142 and 144 indicate where deletions have occurred or have been constructed from the parent Htk+ gene.

The construct of FIG. 5 is only one of many within the scope of this invention which can utilize at least two nonfunctional alleles. Thus, by way of illustration and not limitation, alleles 136 and 138 may be Hprt–, neo–, hph–, Xgpt–, hyg– and the like. Thus, by way of illustration and not limitation, the spacer DNA 140 may be any DNA sequence but it is not essential for the system and thus it might be omitted without adverse affects.

In the construct of FIG. 5, a selectable gene must be present. Thus, referring to FIG. 5, construct 134 contains two nonfunctional Htk– alleles so that the cell line is unable to grow in the presence of hypoxanthine, aminopterine and thymidine (HAT medium). If one were to substitute Hprt– for the Htk– allele, the cell line would also be unable to grow on HAT medium. If one were to substitute neo– (coding for neomycin resistance in bacteria) for the Htk– allele, the cell line would be unable to grow on medium containing G418. If one were to substitute hph– or the hyg– gene (coding for hygromycin B phosphotransferase) for the Htk+ allele, the cell line would be unable to grow on medium containing hygromycin B. If one were to substitute Xgpt– (coding for bacterial xanthine guanine phosphotransferase) for the Htk– allele, the cell line would be unable to grow on medium containing guanine and mycophenolic acid.

Construct 134 spontaneously undergoes genome rearrangement under ambient conditions to produce construct 146. It should be noted that this rearrangement involves the unequal pairing of the Htk– alleles, each one residing on one sister chromatid after DNA replication. After pairing, these alleles recombine with each other to yield construct 146. The rearrangement occurs at a certain rate under ambient conditions, but the rate of the rearrangement is expected to be increased if the cell would grow in the presence of many DNA damaging agents.

Construct 134 is unable to grow in the presence of the aforementioned substances. The genome rearrangement which is expected to be favored by the presence of the DNA-damaging agents forms construct 146 which is able to grow in the presence of the aforementioned substances or whatever alleles 136 and 138 are unable to grow in the presence of.

Unlike the constructs produced in FIGS. 3 and 4, the arrangement of alleles in construct 146, after the genome rearrangement, is comprised of the HTK allele 148 flanked by a duplication 150 and 152 of a portion of construct 134. It is believed that the rearrangement which occurs in this case involves unequal sister chromatid exchange or unequal sister chromatid conversion.

Figure 6:
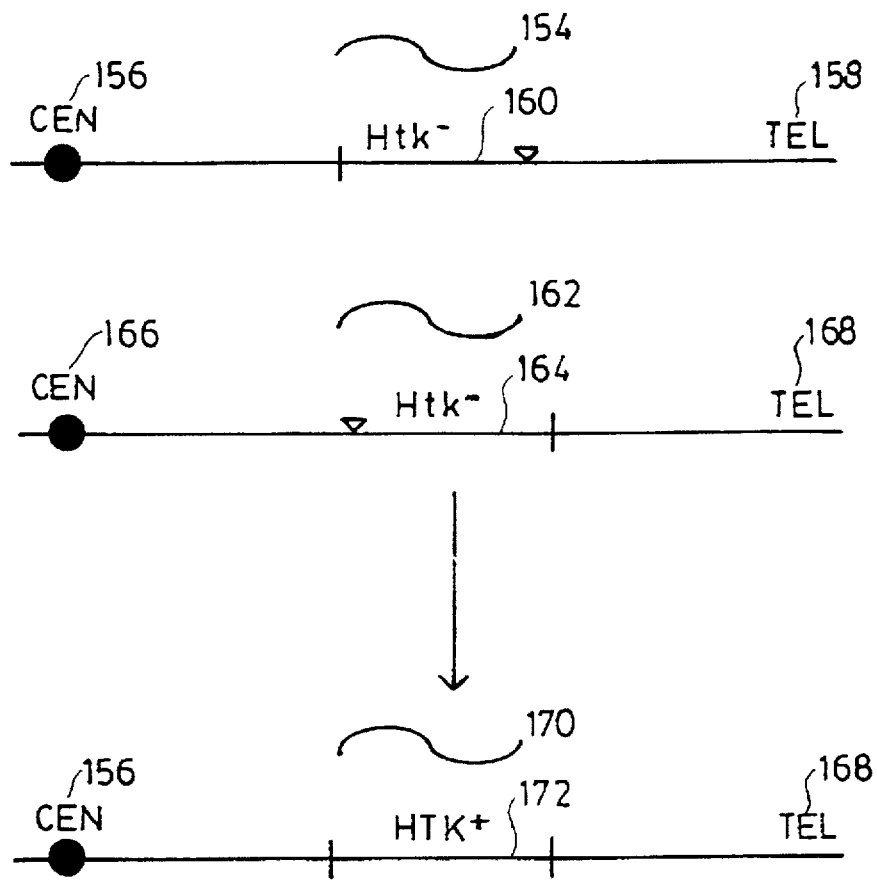

FIG. 6 illustrates yet another embodiment involving two homologous alleles which, unlike the constructs of FIG. 3, 4, and 5, each reside on different, non-homologous chromosomes. Referring to FIG. 6, chromosome 154 is comprised of centromere 156 and telomere 158. As those in the art are aware, the term centromere refers to the spindle fiber attachment region of a chromosome. The term telomere refers to the region forming each end of the chromosome.

Referring again to FIG. 6, chromosome 154 is comprised of Htk– allele 160. Non-homologous chromosome 162 is comprised of Htk– allele 164, centromere 166, and telomere 168. The chromosomes 154 and 162 are nonhomologous; the alleles 160 and 164 are homologous and undergo recombination to give rise to the wild type HTK allele 172 on the hybrid chromosome 170, which comprises centromere 156 from chromosome 154 and telomere 168 from chromosome 162. This mechanism is known to those skilled in the art as translocation.

As is the case with the constructs of FIG. 5, one can use other alleles of genes Hprt, neo, hph (hyg), Xgpt, and the like. Any nonhomologous chromosome pair can be used to provide chromosomes 154 and 162.

The medium used in any particular situation wherein the construct of FIG. 6 will be used in the process should be the respective medium selecting against the alleles used. If, e.g., alleles 160 and 164 are Htk–, then a selection medium should contain hypoxanthine, aminopterine and thymidine. If, e.g., alleles 160 and 164 are neo–, then the selection medium should contain G418, etc.

Cells containing the constructs 154 and 162 are unable to grow in the presence of the respective factor(s). However, cells containing the construct 170 formed by the rearrangement are able to grow in the presence of the respective factor(s).

Figure 7:
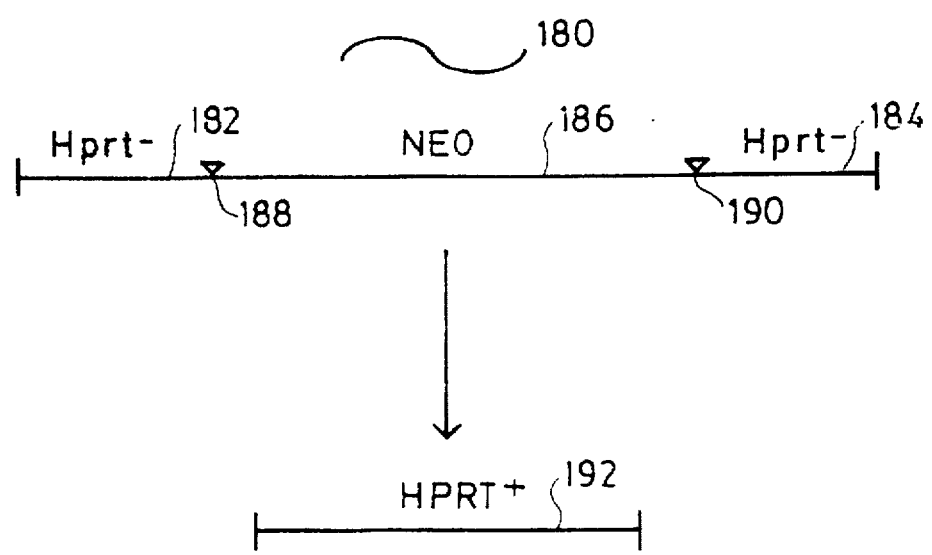

FIG. 7 illustrates one class of homologous elements which can be present in the mammalian cells used in applicant's process. Referring to FIG. 7, construct 180 is comprised of Hprt– allele 182, the homologous Hprt– allele 184, and the NEO gene 186. Points 188 and 190 indicate where deletions have been constructed in vitro from the parent HPRT gene. Because of the deletions constructed at points 188 and 190, alleles 182 and 184 are non-functional; however, when they recombine, they form the functional HPRT+ gene 192.

The construct of FIG. 7 is only one of many within the scope of this invention which can utilize at least two nonfunctional alleles. Thus, by way of illustration and not limitation, alleles 182 and 184 may be tk–, neo–, hph– (hyg–), Xgpt–, and the like. Thus, by way of illustration and not limitation, the NEO gene 186 may be replaced by HPRT, TK, HPH (HYG), XGPT, and the like.

In the construct of FIG. 7, mutant alleles must be present. As used in this specification, a mutant allele is a mutation which causes the cell line to be sensitive to certain factor(s) to which the same cell line with a wild type allele would be resistant. Thus, referring to FIG. 7, construct 180 contains two nonfunctional Hprt– alleles which cause the cell line to be unable to grow in the presence of hypoxanthine, aminopterine and thymidine. If one were to substitute neo– for the Hprt– allele, the cell line would be unable to grow in the presence of G418.

Referring again to FIG. 7, gene 186 should be a wild type allele, i.e., when the system used in applicant's invention is constructed, gene 186 is selected for to give rise to construct 180. In this process, a wild type allele is disrupted. By way of illustration, as shown in FIG. 7, the HPRT gene is disrupted. This selection process will be illustrated later in this specification and can be carried out with any other selectable wild type gene such as TK and the like.

The construction of construct 180 and a cell line harboring that construct has been published by Thomas and Capecchi in Cell (1987) volume 51 on pages 503–512 and is available to those skilled in the art.

Construct 180 should spontaneously revert to its respective wild type gene 192 under ambient conditions. Thus, for example, the cell line containing construct 180 illustrated in FIG. 7 should revert to the HPRT+ wild type gene 192 at an expected frequency of more than $1 \times 10^{-11}$ occurrences per cell. One of the unique expected advantages of construct 180 is that, when the cell line containing construct 180 is growing in the presence of a nonmutagenic carcinogen, the rate of reversion to its wild type gene 192 increases substantially.

A very preferred class of constructs for use in applicant's process are those described in FIG. 3 and FIG. 7 and in that portion of the specification which corresponds to FIG. 3 and FIG. 7.

During the prosecution of U.S. Pat. No. 5,273,880 (the entire disclosure of which and the entire file history of which is hereby incorporated by reference into this specification), a declaration was filed by Dr. Paul Ponath on or about Jul. 16, 1993. This declaration discloses the construction of repeated genetic elements in a human cell line. The techniques disclosed in this declaration, and in other portions of this specification, may be used to construct repeated genetic elements in a mouse embryonic stem cell line.

Referring again to FIGS. 3–7, the constructs of such Figures are used to detect the presence of chemicals which cause genome rearrangement. The cells used in this embodiment are embryonic stem cells. Transgenic mice are produced from such cells by conventional means such as, e.g., those disclosed on pages 255–272 of the aforementioned Watson et al. book ("Recombinant DNA"), and/or those disclosed in A. Gossler et al. in an article entitled "Transgenesis by means of blastocyst-derived embryonic cell lines (published in Proceedings of the National Academy of Science USA, 83:9065–9069 (1986). Reference may also be had to U.S. Pat. Nos. 4,736,866 and 5,087,571, the disclosures of which are hereby incorporated by reference into this specification.

By way of further illustration, reference also may be had to an article by S. L. Mansour et al. ("Disruption of the proto-oncogene-int-1 in mouse embryo-derived stem cells: a general strategy for targeting mutations to nonselectable genes", Nature 336:348–352, 1988). The isolation of the embryonic stem cells from mouse blastocysts may be carried out by a process in which mice a first mated and, three days later, blastocysts are isolated and cultured in petri dishes. The cells spread out over the surface of the dish so that the clump of cells forming the inner cell mass, and corresponding to the future embryo, can be removed. The clump of cells is dissociated into single cells using trypsin, a proteolytic enzyme. If embryonic stem cells are plated out of a plain culture surface, they will differentiate into a variety of tissues; but if they are grown on a feeder layer of fibro blasts, they will continue to proliferate and can be subcultured repeatedly. A feeder layer is a monolayer of cells that has been treated so that the cells no longer divide. They continue to metabolize and, in so doing, condition the culture medium so that the cells seeded on top of them survive and grow better.

Thus, as is illustrated by these references, construct 110 (or any of the other constructs shown in FIGS. 3 to 7) may be introduced into the embryonic stem cells. Those cells that contain the construct are selected as described elsewhere in this specification. The cells are then microinjected into a blastocyst, where they will become assimilated into the inner cell mass and take part in the formation of many tissues of the chimeric mouse. The embryonic stem cells and the recipient blastocysts are preferably derived from mice with different coat colors so that the contribution of the embryonic stem cells to the chimeric offspring can be assessed simply by looking at their coat color.

FIGS. 8a, 8b, and 8c are photomicrographs of the follicles of six-day old offspring of the C57/BL-6J mice described elsewhere in this specification, with 100-fold magnification. In general, the process illustrated in FIG. 2 was used to prepare such mice, with certain modifications. In the first place, the pregnant dams were exposed to the agent to be tested at about the 17th day after conception. In the second place, the offspring were sacrificed at about the 6th day after birth, and the fur of the offspring was prepared as described more fully in the Examples of this specification.

FIG. 8a is a photomicrograph of the follicles of unexposed, "wild-type" C57/BL-6J mice. It will be noted that melanin production in the follicles is clearly visible, evidenced as dark black areas in such follicles.

FIG. 8b is a photomicrograph of the follicles of unexposed, mutant (pink eyed dilution unstable) C57/BL-6J mice. It will be noted that melanin production in the follicles is lacking.

FIG. 8c is a photomicrograph of the follicles of exposed, mutant (pink eyed dilution unstable) C57/BL-6J mice. It will be noted that events have occurred in several of the follicles which now show black melanin production in such follicles.

FIGS. 8d, 8e, and 8f are photomicrographs of the hair shafts of six-day old offspring of the C57/BL-6J mice described elsewhere in this specification, with 100-fold magnification. In general, the process illustrated in FIG. 2 was used to prepare such mice, with the aforementioned modifications.

FIG. 8d is a photomicrograph of the hair shafts of unexposed, "wild-type" C57/BL-6J mice. It will be noted that melanin production in the hair shafts is clearly visible, evidenced as dark black melanosomes in such hair shafts.

FIG. 8e is a photomicrograph of the hair shafts of unexposed, mutant (pink eyed dilution unstable) C57/BL-6J mice. It will be noted that melanin production in the melanosomes of such hair shafts is lacking.

FIG. 8f is a photomicrograph of the hair shafts of exposed, mutant (pink eyed dilution unstable) C57/BL-6J mice. It will be noted that events have occurred in several of the hairs the hair shafts of which now show a number of black melanosomes.

Rearrangements between repeated elements in human DNA

The process described elsewhere in this specification which utilizes mice is a highly sensitive biomarker for the detection of ionizing radiation and chemical carcinogens; and such process also may utilize cells isolated from human beings and function as a quantitative assay to determine the level of recombination events between repeated elements in humans.

In the first step of this process, suitable genetic loci useful as biomarkers of intrachromosomal recombination events are identified. In the second step of the process, the assay is utilized to quantify deletion recombination events which are applied directly to screen for spontaneous recombination events occurring in a normal population and to screen for induced recombination events which may occur in populations exposed to different levels of ionizing radiation or other DNA damaging agents or to detect inter-individual variations. The basic concept of this process is to identify gene duplications or dispersed repeated elements that are close together on the same chromosome and to design primers outside of each copy in the unique sequence so that by PCR a fragment can be amplified only after a recombination event between the two copies. In the case when the repeated element is too big in size, any difference in the sequence of the two copies can be used to place a primer within the duplication so that it hybridizes to only one of the two homologous sequences and to place the second primer in a unique sequence on the other side of the second repeat. Alternatively, if the duplicated region is still within the size range that can be amplified any restriction site in the sequence between the two repeated elements can be utilized to eliminate the template of the duplication before amplification.

The process may be used on cell lines, preferentially on relatively normal unrearranged cell lines with and without exposure to ionizing radiation. It is preferred that, once a fragment of the appropriate size has been amplified, this fragment is then partially sequenced using the same primers to prove the identity of the fragment. It is preferred to utilize loci where carriers of the deletion allele are available as positive controls (as in case of rearrangement of the globin gene duplication discussed below) and cell lines may be established from these carriers that can be used as positive control. Once these conditions are established a quantitative PCR approach is then used to determine the level of the recombination product in cell lines exposed or not exposed to ionizing radiation or chemical toxins. As will be apparent to those skilled in the art, this assay is also useful in molecular epidemiology studies.

FIGS. 9-11 are schematics of repeated genetic elements used in one embodiment of applicant's process. In this embodiment, applicant has chosen three loci of repeated sequences (Alu 3 and THE-1 repeats and the globin genes) for to quantify rearrangement events. It will be appreciated that these loci are merely illustrative, and that many other loci also may be used in the process.

Referring to FIG. 9, it will be seen that the upstream region of the human alpha 2-globin gene carries an Alu repeat sequence, Alu 3, comprised of successive insertions of a 300-bp-long, single Alu repeat; it is believed that this insertion occurred during evolution (see, e.g., A. D. Bailey et al., "Sequential insertion of Alu family repeats into specific genomic sites of higher primates," Proceedings of the National Academy of Science USA, 90, 7205-7209, 1993). Both repeats are flanked by short direct repeats. PCR amplification of the DNA region spanning the two repeats produces an amplified product of nearly 743 bp as shown in the FIG. 9. Deletion recombination events involve either the two short direct repeats flanking the Alu 3 DNA or the two Alu 3 repeats themselves. Deletion events occurring within the regions flanked by the designed primers appear as DNA fragments of smaller size (about 500 bp or less) depending on the site of the breakpoint.

As will be apparent to those skilled in the art, suit able primers may be designed for the PCR amplification. In one embodiment, oligonucleotide primers are custom synthesized. In one embodiment, not shown, a homology search of the primers against the genome showed sequence specificity only for the psi alpha 1-alpha 2 globin intergenic region (see FIG. 9), suggesting that random priming may be unlikely.

It is preferred that PCR conditions be initially adjusted to amplify the 743 bp DNA from wild type DNA isolated from an established human cell line. Cells are then exposed to ionizing radiation in vitro and the DNA analyzed for deletion events occurring in the Alu 3 repeat region using suitable primers. After analyzing the spectra of deletion events occurring in vitro. PCR conditions are then modified so as to allow amplification of only the recombination products (smaller in size) and not the wild type sequence. This allows one to visualize deletion events occurring at low rates. Additionally, the sequence between the two Alu sequences preferably are searched for any cutting sites of restriction enzymes that can be used to destroy the duplication template.

In one preferred embodiment, a similar approach is applied to other Alu repeats in the genome. A doublet of Alu 1 repeats lies between alpha 1 and theta 1 globin loci, as two direct repeats flanked by the same short repeats present in the alpha 2 upstream region.

Referring to FIG. 10, it will be seen that the THE-1 sequences can advantageously be used in applicant's process. These THE-1 sequences are repetitive elements occurring at about 10,000 times in the genome; similar (but not necessarily identical) transposable elements occur in other mammalian species. Referring again to FIG. 10, it will be seen that these THE-1 elements have a length of about 1600 bp and are flanked by LTR sequences of 350 bp in size (see the article by Paulson et al., 1985, supra). It has been reported that two introns of the human dystrophin gene, introns 7 and 44, are associated with deletion events. A cluster of two THE-1 and three isolated LTR sequences are located near the postulated breakpoint regions in the intron 7 of the dystrophin gene (see J. C. McNaughton et al., Journal of Molecular Biology, 232, 314–321, 1993), suggesting that such sequences are involved in recombination events in the genome. The two THE-1 repeats, 2.3 kb each, are arranged in opposite orientations and separated by about 20 kb DNA. Both THE-1 elements and the three LTRs are flanked by short 5 bp direct repeats. The dystrophin gene located at Xp21.2 on X chromosome is 2300 kb long and codes for a muscle protein, dystrophin.

FIG. 10 shows the location of a THE-1 element near one of the translocation breakpoint regions present on the dystrophin gene, observed in a case of Duchenne Muscular Dystrophy (DMD) disease (see S. E. Bodrug et al., "Molecular analysis of constitutional X-autosome translocation in a female with muscular dystrophy," Science 237, 1620–1624, 1987). The element itself is flanked by LTRs of about 350 bp in size. McNaughton et al. (1993, supra) have described a PCR approach to detect this THE-1 repeat as well as one of the flanking LTR regions (5'-LTR).

In one embodiment, the same primers reported in the McNaughton et al. study are used either along or with one or more new primers to quantify the recombination deletion events occurring at this locus. Referring to FIG. 10, it will be seen that the primers of the McNaughten et al. paper are homologous to sequences at positions 1, 2, 3, and 4, respectively.

PCR amplification of normal human DNA isolated from a wild type cell line using the McNaughten et al. primers at positions 1 and 3 (see FIG. 10) produces a 2.58 Kb DNA fragment containing the entire THE-1 element, while the primer at positions 1 and 2 produces a 0.56 kb DNA spanning the 5'-LTR sequence of the THE-1 element. A combination of primer 4 and 3 span a larger segment of DNA of about 3.43 kb in size which is difficult to amplify from the wild type DNA due to the difficulty of amplifying such large DNA sequences by PCR method. Deletion recombination events occurring within the LTR sequences of this THE-1 element are visualized as smaller PCR reaction products of around 1.4 kb using this primers 4 and 3. Primers 1 and 3 also give shorter amplification products as a result of intras-trand recombination events. As described previously, cells are exposed to ionizing radiation and/or chemical toxins, and the deletion spectra at the THE-1 locus located in the intron 7 region of the dystrophin gene is quantified.

FIG. 11 is a schematic of the fetal gamma globin gene duplication. The human beta-globin gene cluster consists of five linked genes coding for one embryonic (epsilon), two fetal, and two adult globin genes, and the genes are arranged in a 60 kb DNA region on chromosome 11 in the order of their developmental expression. One pseudogene is located between the embryonic and the fetal genes. The human beta-globin gene cluster is a well characterized locus and the nucleotide sequence of all the five genes in the cluster has been determined (see F. E. Baralle et al., "The primary structure of the human epsilon globin gene," Cell 21, 621–626, 1980). The globin genes are present in multiple copies in different species, suggesting gene duplication events of a common ancestral gene through evolution. The beta-globin gene locus is characterized by frequent genome rearrangements including deletion events, possibly due to the clustering of highly homologous DNA regions. The 5' region of the cluster beginning upstream of the epsilon gene and extending 5' to the psi-beta globin gene spans a 34.6 kb region whereas the 3' cluster including sequences 5' to the delta globin gene and extending to the 3' of the beta globin gene consists of a 19.4 kb DNA fragment. The 9.1 kb region in between these two segments of the globin gene cluster has been recognized as a hotspot region for germline recombination, leading to various genetic disorders in the affected individuals, such as Hemoglobin Lepore (delta—beta fusions), Hemoglobin Kenya genes (fetal gene—beta globin gene fusions), etc. The genetic rearrangements are thought to occur by homologous but unequal crossing over events.

Nucleotide analysis shows that the two fetal globin genes are located within a region containing a 4.9 kb tandem duplication (S. Shen et al., "A history of the human fetal globin gene duplication, Cell 26, 191–203, 1981), an event which was followed by a gene conversion event spanning a region of 1.5 kb in size. Many differences in the nucleotide sequence exist between the two duplicated segments of the globin genes.

Deletion events occur in somatic cells as well, possibly at a low spontaneous frequency in the normal population. Thus, in one embodiment, one quantifies possible recombination products of rearrangement events involving the two duplicated fetal globin gene clusters, using a PCR based DNA screening method.

FIG. 12 is a schematic of the cDNA of the pink-eyed dilution gene. As will be apparent to those skilled in the art, the PCR method also may be used to detect and quantify rearrangement events in the aforementioned pink eyed dilution locus in the mouse. It has been shown that spontaneous reversion of the p$^{un}$ mutation to wildtype is due to intrachromosomal recombination (see Gondo et al. 1993, supra).

By genome scanning and molecular cloning techniques, the p$^{un}$ DNA was shown to carry a head to tail tandem duplication of ~75 kilobases, and the loss of one copy of the duplicated DNA was shown to be associated with the reversion phenotype in a spontaneous revertant mouse (Gondo et al., 1993, supra; Gardner et al., 1992, supra). The reversion event occurring in p$^{un}$ mice may be due to a similar mechanism, whereby, one copy of the 75 kb duplicated segment in p$^{un}$ DNA is deleted by an intrachromosomal recombination event. This has been shown by Southern blotting (Gondo et al. 1993) as difference between a revertant mouse strain and the p$^{un}$ mutant. For the molecular detection of reversion events in spots this is not possible. First, the spots are rather small and the chance is very minimal that they will enter the germline. Secondly, because of the small size, Southern blotting is very difficult to carry out if not impossible. PCR also cannot be used for detection on the genomic level since p$^{un}$ contains a tandem duplication and the primers to detect the revertant would have to be placed on each side of the duplication in the unique sequence and it is not possible to amplify a 75 kb piece of DNA. However, it has been shown that in p$^{un}$ animals the p gene is disrupted and contains a 4.8 kb transcript rather than the 3.3 kb transcript of the wildtype or the revertant (Gardner et al. 1992). Since the duplication in p$^{un}$ animals is an internal duplication of the p gene there must be a novel breakpoint within the RNA in the p$^{un}$ transcript versus the revertant or wildtype.

Applicant conducted an experiment to determine whether the induced reversion events (black spots) in p$^{un}$ homozygous mutant mice on exposure to ionizing radiation is due to the loss of the disrupting DNA duplication, utilizing a method based on Reverse Transcriptase-Polymerase Chain Reaction (RT-PCR. PCR from cDNA), to screen cells for reversion events at the genetic level and producing different PCR fragments in the p$^{un}$ versus the wildtype (see FIG. 12). Using the published sequence for the p gene (Gardner et al., 1992, supra) and with the help of primer design software, applicant designed 16 different primers and carried out RT-PCR reactions using newly isolated RNA. So far he succeeded in identifying one set of primers amplifying a fragment that is specific for the wildtype, even though neighboring and overlapping fragments did amplify from the same RNA preparations. As summarized in FIG. 12, the p$^{un}$ and wild type cDNA differ in the region denoted by 'e'. The expected 238 bp DNA product spanning the region 'e' of p cDNA was not amplified from the p$^{un}$ transcript, suggesting a disruption of the transcript. Product 'g' was co-amplified as an internal control in the experiments, to ensure successful amplification.

In these experiments, seven to nine days old offspring of pun (p$^{un}$/p$^{un}$) as well as wild type (p+/p+) or heterozygote (p±) mice were sacrificed and skin samples were quick frozen in liquid nitrogen. Skin tissues were homogenized using an automated microhomogenizer. Total RNA was isolated using RNAZol reagent (Biotecx Lab. Inc.) followed by mRNA selection using Invitrogen kit, according to the instructions provided by the manufacturer. RT-PCR was carried out on the samples using the various primer sets (custom synthesized from Amitof, Mass.) in different reactions, using GeneAmp RNA PCR kit (Perkin Elmer Cetus, Conn.). In general, 30–35 cycles were performed at annealing temperatures best suited for each sets of primers chosen. An aliquot of the amplification product was separated on agarose gels and visualized under UV light following ethidium bromide staining.

To characterize the phenotypic reversion at the molecular level, an analysis of the RNA expressed by the spotted skin of offsprings of p$^{un}$ mice (exposed to ionizing radiation on day 10.5 of pregnancy) for wild type-specific expression of the pink eyed dilution gene has been carried out. The RNA was prepared as described above and primers spanning region 'e' were used in an RT-PCR reaction to distinguish between wild type and mutant specific transcripts of the p gene, along with the internal control described above. This experiment showed that wild-type RNA could be isolated from the toxin-induced spots on the coats of the mice.

As will be evident to those skilled in the art, this method may also be used as a quantitative PCR approach with serial dilutions to detect an increased frequency of reversion after exposure to ionizing radiation after the 17th day of embryonic development.

The pink-eyed unstable mutation can be transferred onto genetic backgrounds other than C57/BL6J by repeated back crossing with the other mouse strain, in substantial accordance with methods described elsewhere in this specification. In the first step of this embodiment, it is preferred that the new strain of mouse be crossed with the C57/BL-6J wild type strain of mouse until only entirely black offspring are obtained. In the second step of this process, these black offspring containing the new mutation are crossed with the C57/BL-6J pink eyed unstable mutant mice until gray offsprings are obtained. These gray offsprings containing the new mutation may be used in applicant's process.

The aforementioned experiment was conducted by applicant to construct a mouse strain homozygous for each of the 53 disruption mutation and the pink-eyed dilution unstable mutation.

EXAMPLES

The following examples are presented to illustrate the claimed invention and are not to be deemed limitative thereof. Unless otherwise stated, all temperatures are in degrees Centigrade and all parts are by weight.

Example 1

In the experiment of this Example, the process illustrated in FIG. 2 of the specification was used to detect the effect of X-rays upon the frequency of spots upon the coats of pink eyed dilution unstable C57BL/6J mice.

Six C57BL/6J mice homozygous for the pink-eyed dilution unstable mutation were purchased from the Jackson Laboratory of 600 Main Street, Bar Harbor, Me.; three males and three females were purchased.

The mice were bred to establish a colony of about 1,000 mice. The mice so bred were used in the experiments of the examples of this specification.

498 of such offspring mice were used as a control group in the experiment of this example. This control group was not deliberately exposed to any ionizing radiation or chemical toxin.

Mice homozygous for pink-eyed dilution unstable C57BL/6J p$^{un}$/p$^{un}$ were used to determine the frequency of revertant spots on their coat in response to X-ray exposure. The protocol used for this test was similar to the "mouse spot test" described in Russell et al. 1981, supra)

The unexposed offsprings were examined for spots on their coats at 12 to 14 days of age, when spots are most easily visible. Two subsequent examinations were performed, the last one at 4 to 5 weeks after birth. Animal care and experiments were carried out according to institutional guidelines Of such 498 unexposed offsprings mice, twenty-eight of such mice showed spots on their coats. Thus, the frequency of spotting was 5.6% (28/498).

To provide offsprings for the remainder of the experiment of this example, matings were set up between mice homozygous for p$^{un}$, and pregnancy was timed from the discovery of a vaginal plug. First and second litters were used and gave the same results. Sperm entry into the egg was assumed to have occurred in the early morning hours of the day on which the plug was found and the noon time of this day has been defined as 0.5 days post-conception.

At the 8.5th day after conception, the pregnant dams were subjected 1 Gray of X-radiation. Irradiation was conducted with a Westinghouse 150 Industrial X-ray Machine which produced 130 kvp X-rays, delivered by a self-rectifying tube; the X-rays passed through a sheet of aluminum which was 1.65 millimeters thick before they contacted the mice. With a current of 8 milliamperes, the intensity obtained at 40 centimeters distance was about 24 rads per minute.

The mice were exposed while constrained in individual sterile polypropylene/polyethylene containers resting on a 24 centimeter diameter steel turntable. The mice were rotated to ensure a more accurate average value of the irradiated field. The delivered dose was measured for each irradiation with a Victoreen C-r 570 ionization meter.

The offspring of the irradiated examined for spots at 12 to 14 days after birth, and the size and distribution of such spots were recorded. Two subsequent examinations were performed, the last one at 4 to 5 weeks. Animal care and experiments were carried out according to institutional guidelines.

Twenty-three pregnant dams were irradiated in this experiment, and they produced 61 offsprings of which 36 survived. The number of spotted offspring was 9, for a frequency of spotting rate of 25 percent.

Example 2

The procedure of Example 1 was substantially followed, with the exception that 24 pregnant dams were irradiated at 9.5 days after conception. 62 offspring were produced, of which 56 survived. Twelve of such survivors had spots, for a frequency of spotting of 19 percent.

Example 3

The procedure of Example 1 was substantially followed, with the exception that 64 pregnant dams were irradiated at 10.5 days after conception. 174 offspring were produced, of which 172 survived; 40 of such survivors had spots, for a frequency of spotting of 23 percent.

Thus, radiation at the 8.5th day after conception produced substantially more teratogenic effects and mortality than irradiation at the 9.5th or the 10.5th day after conception.

The average frequency of spotting for all of the experiments of Examples 1, 2, and 3 was 23 percent (61/264).

Example 4

The procedure of Example 1 was substantially repeated, with the exception that, instead of being exposed to ionizing radiation, the pregnant dams were exposed to ethyl methane sulfonate.

In this experiment, the control group of mice was bred in the summertime, when there was a relatively high level of humidity in the breeding room, leading to the production of mold in several of the cages. 585 offsprings were used in the control group, and 62 of such offsprings exhibited spots, for a frequency of spotting of 11 percent.

When a dehumidifier was installed in the breeding room, the frequency of spotting decreased to a level of about 5 percent.

21 pregnant dams were injected intraperitoneally with 100 milligrams per kilogram of body weight of ethylmethane sulfonate, which is known to aklylate DNA and is potent carcinogen which tests positively in most mutagenesis assays. The 21 treated dams produced 94 live offspring; of these, 27 exhibited spots, for a frequency of spotting of 29 percent.

Example 5

The procedure of Example 4 was substantially followed, with the exception that 100 milligrams/kilogram of methylmethane sulfonate were used instead of the ethylmethane sulfonate. The methylmethanesulfonate is also a potent carcinogen which also alkylates DNA and is positive in many mutagenesis assays; it is at least as carcinogenic as ethylmethane sulfonate.

22 treated dams produced 83 live offspring, 21 of which exhibited spots. The frequency of spotting thus was 25 percent.

Comparative Example 6

An experiment was conducted by Jon C. Mirsalis et al. with the Stratagene C57BL/6 transgenic mouse; this experiment was reported in an article by Jon C. Mirsalis et al. entitled "Induction of hepatic mutations in lacI transgenic mice." Mutagenesis, volume 8, number 3, pages 265–271, 1993 (see page 266).

In the experiment described in this paper, the mice were injected twenty-one times with daily does of 20 milligrams per kilogram of body weight of methylmethane sulfonate; thus, the cumulative amount of the mutagen administered to the mice was 420 milligrams per kilogram, which is about four times the amount administered in the experiment of Example 5.

Mirsalis et al. reported that " . . . MMS (20 mg/kg/day) failed to increase the mutant frequency . . . ."

Example 7

The procedure of Example 4 was substantially followed, with the exception that 25 milligrams/kilogram of ethylnitroso urea were used instead of the ethylmethane sulfonate. The ethylnitrosourea is also a- potent carcinogen which is a mutagen and is positive in many mutagenesis assays.

18 treated dams produced 57 live offspring, 30 of which exhibited spots. The frequency of spotting thus was 53 percent.

Example 8

In this experiment, the toxic material tested (benzo[a] pyrene) was administered in mixture with corn oil solvent.

A control group of 10 pregnant dams was injected with 0.2 milliliters of corn oil per mouse. The dams so treated produced 51 live offspring, 2 of which exhibited spots. The incidence of spotting in the control group was 3.9 percent.

A mixture of 150 milligrams of benzo(a) pyrene per kilogram of mouse body weight in 0.2 milliliters of corn oil per mouse was injected into 10 pregnant dams; benzo(a) pyrene is produced by pyrolysis of fat such as is produced, e.g., by the frying of hamburgers; it is a very prevalent chemical, and it is known to be carcinogenic to animals as well as humans. Thirty-two live offspring were produced from such dams, 20 of which exhibited spotting. The incidence of spotting was thus 63 percent.

Example 9

The procedure of Example 8 was substantially repeated, with the exception that 200 milligrams of trichlorethylene per kilogram of mouse body weight in mixture with 0.2 milliliters of corn oil were administered to 18 pregnant dams; trichloroethylene is a widely used commercial solvent which, according to the Environmental Protection Agency, is one of the ten most dangerous chemicals. The dams so treated produced 41 live offspring, 13 of which exhibited spots. The incidence of spotting was 32 percent.

Trichloroethylene is a nonmutagenic material which, thus, produces a negative response in the widely-used Ames test.

Example 10

The procedure of Example 8 was substantially repeated, with the exception that 200 milligrams of benzene per kilogram of mouse body weight in admixture with 0.2 milliliters of corn oil were administered to 15 pregnant dams. Benzene is a very widely used commercial solvent which several years ago was discovered to be a human carcinogen; however, it is negative in the Ames test. Prior to that time it was widely used in many laboratories without adequate safeguards.

The dams so treated produced 48 live offspring, 13 of which exhibited spots. The incidence of spotting was 27 percent.

Example 11

In this experiment, the toxic material tested (sodium arsenate) was administered in mixture with 0.2 milliliters of water.

A control group of 337 offsprings, which were born to pregnant dams which were not injected with sodium arsenate, had 18 incidents of spotting, for a frequency of spotting of 5.3 percent.

20 milligrams of sodium arsenate per kilogram of body weight of the mouse, in mixture with 0.2 milliliters of water, were injected into 17 pregnant dams. Sodium arsenate is a human carcinogen, but it is not detectable by the Ames Assay. The Environmental Protection Agency rates it as being the second most dangerous chemical.

Fifty-six offspring were born the pregnant, 16 of which exhibited spotting, for a frequency of spotting of 29 percent.

Example 12

The procedure of Example 1 was substantially followed, with the exceptions that the treatment occurred at 17.5 days after conception, the frequency of follicles or hair shafts on each offspring mouse containing black melanin was determined (see FIG. 8).

The experiment of this Example using single hairs was carried in substantial accordance with the procedure set forth in the specification with regard to FIGS. 8a–8f.

Six unirradiated offsprings were from 3 independent litters were used as control group. The skin of the mice was prepared as described by Searle and Stephenson, supra (1982). The animals were sacrificed by decapitation 6 days after birth, blood was allowed to drain away, and each mouse was dissected to remove the skin. The skins were then treated with 10% formalin for at least 24 hours, washed in distilled water and transferred to 70% ethanol for 24 hours, and then transferred to 90% ethanol for 24 hours followed by two changes of absolute ethanol 12 hours each. The skins were then treated with a 1:1 benzyl/ethyl alcohol mixture for 12 hours and with pure benzyl alcohol for 12 hours. With blunt end forceps any adherent muscle tissue was removed to leave the skin as thin as possible. The skin was then divided into 12 dorso-lateral segments and each segment was mounted in Canada Balsam with the dorsal surface upper most on a microscopic slide under a cover slip. The slides were then left to dry on a hot plate at 40° C. Each slide was examined in a bright field under 100 fold magnification and the follicles and hair counted.

In the control experiment of this Example, 3,906 hair follicles were examined. Forty-five of such follicles were pigmented, for an incidence of pigmentation of 1.15 percent in the control group.

In another experiment, six litters of mice were used to produce 12 offspring. The six pregnant dams were irradiated at the 17.5th day with 1 Gray of X-radiation in accordance with the procedure of Example 1. 7,512 follicles were examined on the 12 offspring of the irradiated dams, and 1,053 pigmented follicles were found, for incidence of pigmentation of 14.0 percent. Thus, there was a 1200 percent increase in pigmentation between the irradiated group and the control group.

Example 13

The procedure of Example 12 was substantially followed, with the exception that the hair shafts rather than the hair follicles of the offspring mice were counted.

In the control group, 8 pregnant dams produced 15 offsprings, and 12,218 hair shafts were counted. 135 of the hair shafts so counted were pigmented, for an incidence of pigmentation of 1.1 percent.

In a separate experiment, 5 pregnant dams were irradiated with 1 centiGray, and they produced 13 offspring. 16,812 hair shafts were examined on these offspring, and 595 incidents of pigmentation were noted, for a percent pigmentation of 3.6 percent.

Thus, even for the relatively modest dose of 1 centiGray (which is not detectable by any other biological assay system), and increase in pigmentation of 330 percent was noticed.

Example 14

The procedure of Example 13 was substantially repeated, with the exception that the radiation dose was 6 centiGray. The incidence of pigmentation was 5.1 percent.

Example 15

The procedure of Example 13 was substantially repeated, with the exception that the radiation dose was 9 centiGray. The incidence of pigmentation was 5.0 percent.

Example 16

The procedure of Example 13 was substantially repeated, with the exception that the radiation dose was 35 centiGray. The incidence of pigmentation was 6.8 percent.

Example 17

The procedure of Example 13 was substantially repeated, with the exception that the radiation dose was 50 centiGray. The incidence of pigmentation was 8.3 percent.

Example 18

The procedure of Example 13 was substantially repeated, with the exception that the radiation dose was 75 centiGray. The incidence of pigmentation was 8.3 percent.

Example 19

The procedure of Example 13 was substantially repeated, with the exception that the radiation dose was 100 centiGray. Six pregnant dams were irradiated, and 12 offspring were produced and evaluated. 6,609 hair shafts were counted, of which 802 exhibited pigmentation. Thus, the pigmentation rate was 12.3 percent, which is approximately 1,120 percent higher than the pigmentation rate of the control group.

It thus appears that the assay of this invention is substantially more sensitive than prior art assays. In the experiment of Example 19, at the 17.5th day post conception, the melanocytes should already have migrated into the follicles. Clusters of follicles with revertant melanocytes were excluded from my calculation since these seem to be due to spontaneous events that happened before the 17.5th day post-conception. Thus, it can be assumed that each hair with one reversion event constitutes an independent event. Since I cannot calculate the exact number of revertant melanocytes per follicle, I can only estimate a minimum frequency of one revertant melanocyte per average number of melanocytes per follicle. Since one follicle contains an average of 13.6 melanocytes (Searle and Stephenson, 1982, supra) the minimum frequency of induced reversion events is roughly 1%, or $1 \times 10^{-4}$ induced events per cGy. By comparison, the "specific locus test" gave about $2.2 \times 10^{-7}$ induced mutations per cGy of X-rays (see W. L. Russell, "An augmenting effect of dose fractionation on radiation induced mutation rate in mice," Proceedings of the National Academy of Sciences, U.S.A., 48:1724–1727, 1962) and forward mutations have been determined to be about $2 \times 10^{-6}$ per melanocyte per cGy in a cell based version of the "mouse spot test" (Stephenson and Searle 1988, supra). Thus, the induced frequency of $p^{un}$ reversion is at least 100 fold higher per cGy than forward mutation frequencies and therefore $p^{un}$ reversion may constitute a more sensitive assay.

Example 20

The procedure of Example 13 was substantially followed, using the same control group and data, with the exception that chemical toxins rather than ionizing radiation was evaluated.

In the experiment of this Example, the mice were injected with 100 milligrams per kilogram of body weight of methylmethane sulfonate. Two pregnant dams were injected, 5,001 hairs were counted on the offspring produced, and 521 pigmented hairs were noticed; the pigmentation rate was thus 10.6 percent, which is 960 percent greater than the rate of the control group.

Examples 21–26

The procedure of Example 20 was substantially repeated, with the exception that the methylmethanesulfonate was replaced with ethylmethanesulfonate, benzo(a)pyrene, benzene, trichloroethylene, and sodium arsenate. These materials exhibited a frequency of pigmentation which was 1600 percent, 1500 percent, 540 percent, 1200 percent, and 1500 percent greater than the untreated control samples, respectively.

Example 27

The procedure of Example 20 was substantially repeated, with the exception that the methylmethanesulfonate was replaced with 1,000 milligrams per kilogram of mouse body weight of carbon tetrachloride. Three pregnant dams were injected, and 10,593 single hairs were counted on 9 offspring. It was found that 426 of these hairs were pigmented, for a pigmented rate of 4.1 percent. This pigmentation rate was 290 percent greater than the pigmentation rate of the control sample.

In one preferred embodiment, a mammal's suitability for applicant's process can be determined by evaluating its response to two known toxic agents.

At least 10 of the candidate mammals are first exposed to 1 centiGray of ionizing radiation (see Example 13), and at least 10 of the candidate mammals in a control group are not exposed to such radiation. If the incidence of genome rearrangement which occurs in the the group exposed to radiation is at least 1.2 times as great as the incidence of genome rearrangement occurring in the control group, the candidate mammal has passed the first test in this embodiment.

Thereafter, at least ten of the candidate mammals are first injected with 100 milligrams per kilogram of body weight of methylmethane sulfonate, and at least 10 of the candidate mammals in a control group are not so injected with this toxin. If the frequency of genome rearrangement in the group of mammals injected with methylmethane sulfonate is at least 1.2 times as great as the frequency of genome rearrangement of the mammals in the control group, the candidate mammal has passed the second test in this embodiment.

Mammals which pass both of these tests are suitable for use in applicant's process.

It is to be understood that the aforementioned description is illustrative only and that changes can be made in the apparatus, in the ingredients and their proportions, and in the sequence of combinations and process steps, as well as in other aspects of the invention discussed herein, without departing from the scope of the invention as defined in the following claims.

I claim:

1. A process for screening an agent to determine its effect upon the frequency of genome rearrangement in C57BL/6J-$p^{un}$ mice, comprising the steps of:

(a) exposing at least one of said mice to the agent to be tested, thereby providing an exposed mouse;

(b) determining a first frequency of genome rearrangement which exists in a first animal selected from the group consisting of said exposed mouse, its offspring, and mixtures thereof;

(c) determining a second frequency of genome rearrangement which exists in a second animal selected from the group consisting of said mice which have not been exposed to such agent, the offspring of said latter mice, and mixtures thereof; and (d) comparing said first frequency of genome rearrangement with said second frequency of genome rearrangement.

2. The process as recited in claim 1, wherein said first frequency of genome rearrangement is determined in the offspring of said exposed mice.

3. The process as recited in claim 2, wherein said second frequency of genome rearrangement is determined in the offspring of said mice which have not been exposed to said agent.

* * * * *